United States Patent
Kinnick et al.

(10) Patent No.: US 7,109,231 B2
(45) Date of Patent: Sep. 19, 2006

(54) CYCLOHEPT[B]INDOLE DERIVATIVES

(75) Inventors: Michael Dean Kinnick, Indianapolis, IN (US); Edward David Mihelich, Carmel, IN (US); John Michael Morin, Jr., Brownsburg, IN (US); Daniel Jon Sall, Greenwood, IN (US); Jason Scott Sawyer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 359 days.

(21) Appl. No.: 10/483,939

(22) PCT Filed: Jul. 29, 2002

(86) PCT No.: PCT/US02/21299

§ 371 (c)(1),
(2), (4) Date: Jan. 15, 2004

(87) PCT Pub. No.: WO03/016277

PCT Pub. Date: Feb. 27, 2003

(65) Prior Publication Data

US 2004/0198801 A1    Oct. 7, 2004

Related U.S. Application Data

(60) Provisional application No. 60/311,275, filed on Aug. 9, 2001.

(51) Int. Cl.
| | | |
|---|---|---|
| A61K 31/405 | (2006.01) | |
| A61K 31/4045 | (2006.01) | |
| A61K 31/4439 | (2006.01) | |
| A61K 31/5377 | (2006.01) | |
| C07D 413/12 | (2006.01) | |

(52) U.S. Cl. ............ 514/415; 514/339; 514/414; 514/235.2; 544/144; 546/277.7; 548/465; 548/509

(58) Field of Classification Search ............ 514/235.2, 514/339, 414, 415; 544/144; 546/277.7; 548/465, 509
See application file for complete search history.

(56) References Cited

FOREIGN PATENT DOCUMENTS

| EP | 0 950 661 | 10/1999 |
|---|---|---|
| WO | WO 00 07591 | 2/2000 |

OTHER PUBLICATIONS

D. J., Davies, "Mapping the melatonin receptor. 5. Melatonin agonists and antagonists derived from tetrahydrocyclopent 'b!indoles, tetrahydrocarbazoles and hexahydrocyclohept 'b!indoles," *J. Med. Chem.*, vol. 41, No. 4, pp. 451-467 (1998); XP002215114.

*Primary Examiner*—Kamal A. Saeed
*Assistant Examiner*—Jason M. Nolan
(74) *Attorney, Agent, or Firm*—Francis O. Ginah

(57) ABSTRACT

A novel class of tricyclic compounds of the following formula (I): (formula I); is disclosed together with the use of such compounds for inhibiting sPLA$_2$ mediated release of fatty acids for treatment of inflammatory diseases such as septic shock

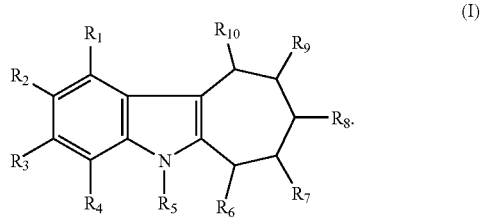

16 Claims, No Drawings

CYCLOHEPT[B]INDOLE DERIVATIVES

This application claims the benefit of Provisional Application No. 60/311,275 filed Aug. 9, 2001.

FIELD OF THE INVENTION

This invention relates to novel tricyclic compounds useful for inflammatory diseases.

BACKGROUND OF THE INVENTION

The structure and physical properties of human non-pancreatic secretory phospholipase $A_2$ (hereinafter called, "sPLA$_2$") has been thoroughly described in two articles, namely, "Cloning and Recombinant Expression of Phospholipase $A_2$ Present in Rheumatoid Arthritic Synovial Fluid" by Seilhamer, Jeffrey.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, issue of Apr. 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds, which inhibit sPLA$_2$ mediated release of fatty acids (e.g., arachidonic acid). Such compounds would be of value in the general treatment of conditions induced and/or maintained by overproduction of sPLA$_2$; such as sepsis, and pain. The treatment of sepsis for example, represents an important unmet medical need for which compounds of the present invention may be used.

SUMMARY OF THE INVENTION

The present invention relates to a compound of formula (I) or a pharmaceutically acceptable salt, solvate or prodrug thereof, useful for the treatment or prevention inflammatory diseases:

alkylcycloheptyl, phenyl, benzyl, methylnapthyl, $(C_1-C_5)$ alkylheterocyclic, carbocyclic radical, or heterocyclic radical, or aryl;

$R_6$, $R_7$, $R_8$, and $R_9$, are each independently selected from hydrogen, or a group containing 1 to 10 non-hydrogen atoms plus any required hydrogen atoms;

$R_{10}$ is selected from an amide or thioamide group represented by the formula,

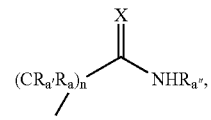

wherein X is oxygen or sulfur, $R_a$ and $R_{a'}$ is independently selected from hydrogen, $(C_1-C_8)$alkyl, or aryl; $R_{a''}$ is hydrogen, $NH_2$, $(C_1-C_8)$alkyl, aryl, $(C_1-C_8)$alkylaryl, or arylalkyl; and n is 0, 1, or 2;

The present invention provides novel tricyclic compounds of formula I having potent and selective effectiveness as inhibitors of mammalian sPLA$_2$.

The present invention also relates to the use of novel tricyclic compounds of formula I useful in the treatment and/or prevention of inflammatory diseases.

This invention also relates to the use of a novel tricyclic compound of formula I to inhibit mammalian sPLA$_2$ mediated release of fatty acids.

The present invention provides a pharmaceutical composition containing any of the tricyclic compounds of the invention.

The present invention also relates to the use of a formulation comprising a compound of formula I, and a carrier or diluent for the treatment or prevention of sepsis.

The present invention relates to the use of a pharmaceutical composition comprising a therapeutically effective amount of sPLA$_2$ inhibitor compounds of formula I and mixtures thereof for the manufacture of a medicament for the treatment of inflammatory diseases.

The present invention relates to the use of a tricyclic compound of formula I for the manufacture of a medicament for the treatment or prevention of inflammatory diseases comprising administering a therapeutically effective amount of a tricyclic compound of formula (I), or a pharmaceutically acceptable salt, solvate or prodrug thereof:

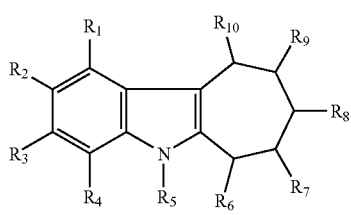
(I)

wherein;

$R_1$ is the group —$(La)$-(acidic group) wherein —$(L_a)$—, is an acid linker having an acid linker length of 1 to 8;

$R_2$, $R_3$, and $R_4$ are each independently selected from non-interfering substituents including hydrogen.

$R_5$ is the group $(C_1-C_{20})$alkyl, $(C_1-C_{20})$haloalkyl, $(C_2-C_{20})$alkenyl, $(C_2-C_{20})$alkynyl, $(C_1-C_{10})$alkylaryl, $(C_1-C_5)$alkylcyclohexyl, $(C_1-C_5)$alkylcyclopentyl, $(C_1-C_5)$

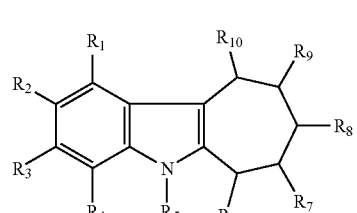
(I)

wherein;

$R_1$ is the group —$(La)$-(acidic group) wherein —$(L_a)$—, is an acid linker having an acid linker length of 1 to 8;

$R_2$, $R_3$, and $R_4$ are each independently selected from non-interfering substituents including hydrogen.

$R_5$ is the group $(C_1-C_{20})$alkyl, $(C_1-C_{20})$haloalkyl, $(C_2-C_{20})$alkenyl, $(C_2-C_{20})$alkynyl, $(C_1-C_{10})$alkylaryl, $(C_1-C_5)$alkylcyclohexyl, $(C_1-C_5)$alkylcyclopentyl, $(C_1-C_5)$ alkylcycloheptyl, phenyl, benzyl, methylnaphthyl, ($C_1$–$C_5$) alkylheterocyclic, carbocyclic radical, or heterocyclic radical, or aryl;

$R_6$, $R_7$, $R_8$, and $R_9$, are each independently selected from hydrogen, or a group containing 1 to 10 non-hydrogen atoms plus any required hydrogen atoms;

$R_{10}$ is selected from an amide or thioamide group represented by the formula,

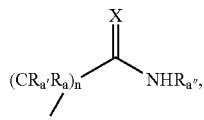

wherein X is oxygen or sulfur, $R_a$ and $R_{a'}$ is independently selected from hydrogen, ($C_1$–$C_8$)alkyl, or aryl; $R_{a''}$ is hydrogen, $NH_2$, ($C_1$–$C_8$)alkyl, aryl, ($C_1$–$C_8$)alkylaryl, or arylalkyl; and n is 0, 1, or 2;

The present invention relates to the use of a compound of formula I for the manufacture of a medicament for the treatment or prevention of inflammatory diseases comprising administering a therapeutically effective amount of a tricyclic compound represented by the formulae (C1), (C2), or (C3):

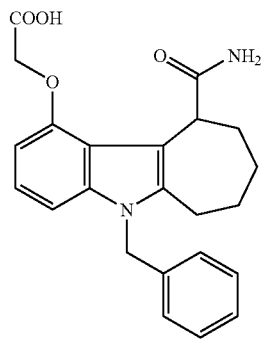

(C1)

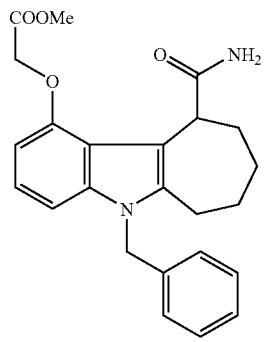

(C2)

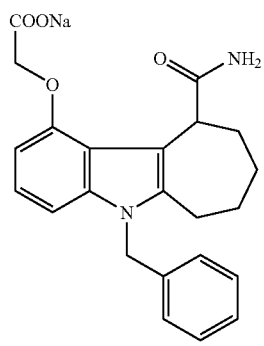

(C3)

I. Definitions:

The terms, "mammal" and "mammalian" include human and domesticated quadrupeds.

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, prostrate cancer, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus eythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The term, "tricyclic", or "tricyclic nucleus" as used herein refers to a nucleus (having numbered positions) with the structural formula (X):

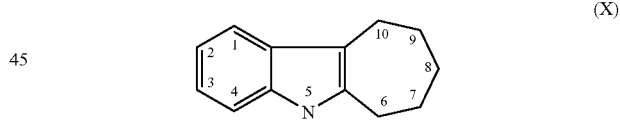

(X)

The tricyclic compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, t-butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, heterocyclic radical, refers to radicals derived from monocyclic or polycyclic, saturated or unsaturated, substituted or unsubstituted heterocyclic nuclei having 5 to 14 ring atoms and containing from 1 to 3 heteroatoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl. phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term "($C_1$–$C_5$)alkylcyclopentyl," "($C_1$–$C_5$)alkylcyclohexyl," or "($C_1$–$C_5$)alkylheterocyclic" represent a ($C_1$–$C_5$)alkyl group attached respectively to a cylopentyl, cyclohexyl, and heterocyclic group wherein the entire group is attached to the tricyclic nucleus (X) at the alkyl terminus. Therefore the mass of the entire group is the mass of the ($C_1$–$C_5$)alkyl group plus the cyclopentyl, cyclohexyl or heterocyclic group to which it is attached.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, benzyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

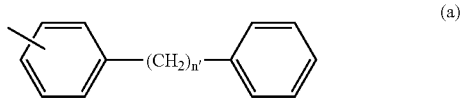

(a)

where n' is a number from 1 to 8.

The term, "non-interfering substituent", or "non-interfering groups" refer to radicals suitable for substitution at positions 1, 2, 3, 4, 5, 6, 7, 8, 9 and/or 10 of the tricyclic nucleus and on other nucleus substituents (as hereinafter described for Formula I), and radicals suitable for substitution on the heterocyclic radical and carbocyclic radical as defined above. Illustrative non-interfering radicals are ($C_1$–$C_8$)alkyl, ($C_2$–$C_8$)alkenyl, ($C_2$–$C_8$)alkynyl, ($C_7$–$C_{12}$)arylalkyl, ($C_7$–$C_{12}$)alkylaryl, ($C_3$–$C_8$)cycloalkyl, ($C_3$–$C_8$)cycloalkenyl, phenyl, benzyl, toluyl, xylenyl, biphenyl, ($C_1$–$C_8$)alkoxy, $C_2$–$C_8$)alkenyloxy, $C_2$–$C_8$ alkynyloxy, ($C_2$–$C_{12}$)alkoxyalkyl, ($C_2$–$C_{12}$)alkoxyalkyloxy, $C_2$–$C_{12}$ alkylcarbonyl, ($C_2$–$C_{12}$)alkylcarbonylamino, ($C_2$–$C_{12}$) alkoxyamino, ($C_2$–$C_{12}$)alkoxyaminocarbonyl, ($C_1$–$C_{12}$)alkylamino, ($C_1$–$C_6$)alkylthio, ($C_2$–$C_{12}$)alkylthiocarbonyl, ($C_1$–$C_8$)alkylsulfinyl, ($C_1$–$C_8$)alkylsulfonyl, ($C_2$–$C_8$)haloalkoxy, ($C_2$–$C_8$)haloalkylsulfonyl, ($C_2$–$C_8$)haloalkyl, ($C_2$–$C_8$)hydroxyalkyl, —C(O)O(($C_2$–$C_8$)alkyl), —(CH$_2$)$_n$—O—($C_1$–$C_8$alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8 and R is ($C_1$–$C_8$)alkyl.

The term, "organic substituent" refers to a monovalent radical consisting of carbon and hydrogen with or without oxygen, nitrogen, sulfur, halogen, or other elements. Illustrative organic substituents are ($C_1$–$C_8$)alkyl, aryl, ($C_7$–$C_{14}$) arylalkyl, ($C_7$–$C_{14}$)alkylaryl, ($C_3$–$C_8$)cycloalkyl, ($C_1$–$C_8$) alkoxyalkyl and these groups substituted with halogen, —CF$_3$, —OH, ($C_2$–$C_8$)alkyl, amino, carbonyl, and —CN.

The term "substituted group" is an organic group substituted with one or more non-interfering substituents.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the tricyclic nucleus have been drawn to show the first line as a connecting bond only. Thus, the group

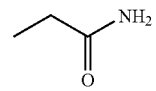

represents the acetamide radical or group, not the propanamide radical unless otherwise indicated.

The term, "(acidic group)" means an organic group which when attached to a tricyclic nucleus at the 1-position, through suitable linking atoms (hereinafter defined as the "acid linker"), acts as a proton donor capable of hydrogen bonding. Illustrative of an (acidic group) are the following:
-5-tetrazolyl,
—SO$_3$H,

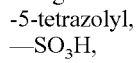

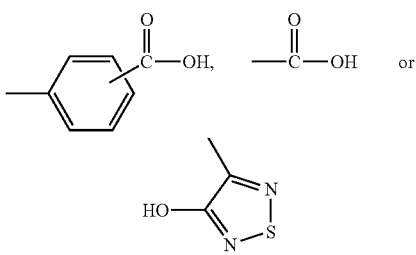

The term, "alkylene chain of 1 or 2 carbon atoms" refers to the divalent radicals, —CH$_2$—CH$_2$— and —CH$_2$—.

The term, "acid linker length" refers to the number groups or atoms directly connecting the tricyclic nucleus to the acidic group.

The term, "group containing 1 to 10 non-hydrogen atoms" refers to relatively small groups which form substituents at the a designated position of the tricyclic nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH═CH$_2$.

The term "spiro[5.5]undecanyl" refers to the group represented by the formula;

II. The Tricyclic Compounds of the Invention:

The present invention provides a novel class of tricyclic compounds useful as sPLA$_2$ inhibitors for the treatment and/or prophylaxis of inflammation attendant to inflammatory diseases.

The compounds of the invention are represented by the general formula (I) and include pharmaceutically acceptable salts, or enantiomers, or solvates thereof;

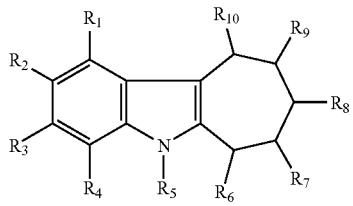

(I)

wherein;

$R_1$ is the group —(La)-(acidic group) wherein —($L_a$)—, is an acid linker having an acid linker length of 1 to 8;

$R_2$, $R_3$, and $R_4$ are each independently selected from non-interfering substituents including hydrogen.

$R_5$ is the group $(C_1-C_{20})$alkyl, $(C_1-C_{20})$haloalkyl, $(C_2-C_{20})$alkenyl, $(C_2-C_{20})$alkynyl, $(C_1-C_{10})$alkylaryl, $(C_1-C_5)$alkylcyclohexyl, $(C_1-C_5)$alkylcyclopentyl, phenyl, benzyl, methylnaphthyl, $(C_1-C_5)$alkylheterocyclic, carbocyclic radical, or heterocyclic radical, or aryl;

$R_6$, $R_7$, $R_8$, and $R_9$, are each independently selected from hydrogen, or a group containing 1 to 10 non-hydrogen atoms plus any required hydrogen atoms;

$R_{10}$ is selected from an amide or thioamide group represented by the formula,

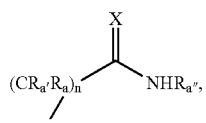

wherein X is oxygen or sulfur, $R_a$ and $R_{a'}$ is independently selected from hydrogen, $(C_1-C_8)$alkyl, or aryl; $R_{a''}$ is hydrogen, NH$_2$, $(C_1-C_8)$alkyl, aryl, $(C_1-C_8)$alkylaryl, or arylalkyl; and n is 0, 1, or 2;

Preferred Subgroups of Compounds of Formula (I):

Preferred $R_1$ Substituents:

A preferred subgroup of $R_1$ is the group —(La)-(acidic group) wherein —($L_a$)—, is an acid linker having an acid linker length of 1 to 8;

Also preferred is a subclass of compounds of formula I wherein —($L_a$)— is an acid linker selected from the group consisting of;

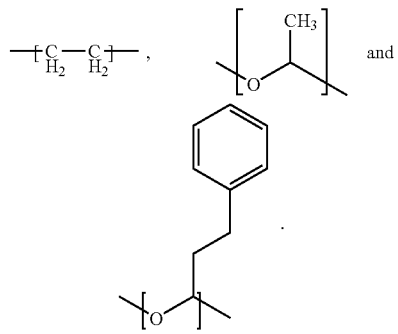

A most preferred subgroup of $R_1$ is the group —(La)-(acidic group) wherein —($L_a$)—, is an acid linker is OCH$_2$;

Preferred $R_2$, $R_3$, and $R_4$

A particularly preferred $R_2$ or $R_3$ or $R_4$ group is a group independently selected from the group consisting of hydrogen, methyl, ethyl, propyl, —OCH$_3$, —OCH$_2$CH$_3$, halogen, phenyl and phenoxy.

Preferred $R_5$ Substituents:

The preferred group for $R_5$ is a substituted or unsubstituted group selected from the group consisting of $(C_5-C_{14})$cycloalkyl, $(C_5-C_{14})$cycloalkenyl, cyclohexylmethyl, cyclopentylmethyl, cyclohexylethyl, phenyl, naphthyl, benzyl, methylnaphthyl, norbornanyl, bicycloheptadienyl, toluyl, xylenyl, indenyl, stilbenyl, terphenylyl, diphenylethylenyl, phenyl-cyclohexenyl, and anthracenyl, biphenyl, bibenzylyl and related bibenzylyl homologues represented by the formula (a);

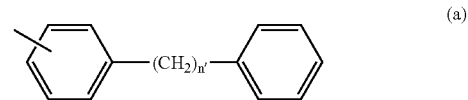

(a)

where n' is a number from 1 to 8.

Most preferred as the group $R_5$ is a group selected from the group consisting of methyl, ethyl, cyclopentylmethyl, cyclohexylmethyl, cycloheptylmethyl, methylnaphthyl, phenyl and benzyl.

Preferred $R_6$, $R_7$, $R_8$, and $R_9$ Substituents:

$R_6$, $R_7$, $R_8$, and $R_9$ are preferably independently selected from the group consisting of hydrogen, $(C_1-C_4)$alkyl, $(C_2-C_4)$alkenyl, —O—($(C_1-C_4)$alkyl), —S—($(C_1-C_3)$alkyl), —$(C_3-C_4)$cycloalkyl, —CF$_3$, halo, —NO$_2$, —CN, —SO$_3$. Particularly preferred $R_7$ groups are selected from hydrogen, methyl, ethyl, propyl, isopropyl, cyclopropyl, —F, —CF$_3$, —Cl, —Br, or —O—CH$_3$.

Preferred $R_{10}$:

A preferred $R_{10}$ is selected from an amide or thioamide group represented by the formula,

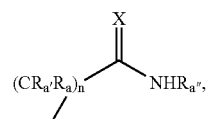

wherein X is oxygen, $R_a$ and $R_{a''}$ are independently selected from hydrogen, and $(C_1–C_8)$alkyl; $R_{a'}$ is hydrogen, $(C_1–C_8)$ alkyl, aryl, $(C_1–C_8)$alkylaryl; and n is 0 or 1.

A more preferred subclass of compounds of formula (I) are those wherein for $R_{10}$, X is oxygen.

Also more preferred is a subclass of compounds of formula I wherein $R_{10}$ is an amide group represented by

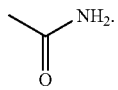

A preferred compound of the invention is a compound selected from the group consisting:
(5-benzyl-10-carbamoyl-5,6,7,8,9,10-hexahydro-cyclohept[b]indol-1-yloxy)-acetic acid,
(5-[(2-phenoxyphenyl)methyl]-10-carbamoyl-5,6,7,8,9,10-hexahydro-cyclohept[b]indol-1-yloxy)-acetic acid,
(5-[(3-phenoxyphenyl)methyl]-10-carbamoyl-5,6,7,8,9,10-hexahydro-cyclohept[b]indol-1-yloxy)-acetic acid,
(5-[(4-phenoxyphenyl)methyl]-10-carbamoyl-5,6,7,8,9,10-hexahydro-cyclohept[b]indol-1-yloxy)-acetic acid,
(5-[(2-fluorophenyl)methyl]-10-carbamoyl-5,6,7,8,9,10-hexahydro-cyclohept[b]indol-1-yloxy)-acetic acid,
(5-[(3-fluorophenyl)methyl]-10-carbamoyl-5,6,7,8,9,10-hexahydro-cyclohept[b]indol-1-yloxy)-acetic acid,
(5-[(4-fluorophenyl)methyl]-10-carbamoyl-5,6,7,8,9,10-hexahydro-cyclohept[b]indol-1-yloxy)-acetic acid,
(5-[(2-chlorophenyl)methyl]-10-carbamoyl-5,6,7,8,9,10-hexahydro-cyclohept[b]indol-1-yloxy)-acetic acid,
(5-[(3-chlorophenyl)methyl]-10-carbamoyl-5,6,7,8,9,10-hexahydro-cyclohept[b]indol-1-yloxy)-acetic acid,
(5-[(4-chlorophenyl)methyl]-10-carbamoyl-5,6,7,8,9,10-hexahydro-cyclohept[b]indol-1-yloxy)-acetic acid,
(5-[(2-bromophenyl)methyl]-10-carbamoyl-5,6,7,8,9,10-hexahydro-cyclohept[b]indol-1-yloxy)-acetic acid,
(5-[(3-bromophenyl)methyl]-10-carbamoyl-5,6,7,8,9,10-hexahydro-cyclohept[b]indol-1-yloxy)-acetic acid,
(5-[(4-bromophenyl)methyl]-10-carbamoyl-5,6,7,8,9,10-hexahydro-cyclohept[b]indol-1-yloxy)-acetic acid,
(5-[(2-iodophenyl)methyl]-10-carbamoyl-5,6,7,8,9,10-hexahydro-cyclohept[b]indol-1-yloxy)-acetic acid,
(5-[(3-iodophenyl)methyl]-10-carbamoyl-5,6,7,8,9,10-hexahydro-cyclohept[b]indol-1-yloxy)-acetic acid,
(5-[(4-iodophenyl)methyl]-10-carbamoyl-5,6,7,8,9,10-hexahydro-cyclohept[b]indol-1-yloxy)-acetic acid,
(5-[(2-acetamidophenyl)methyl]-10-carbamoyl-5,6,7,8,9,10-hexahydro-cyclohept[b]indol-1-yloxy)-acetic acid,
(5-[(3-acetamidophenyl)methyl]-10-carbamoyl-5,6,7,8,9,10-hexahydro-cyclohept[b]indol-1-yloxy)-acetic acid,
(5-[(4-acetamidophenyl)methyl]-10-carbamoyl-5,6,7,8,9,10-hexahydro-cyclohept[b]indol-1-yloxy)-acetic acid,
(5-[(2-carbamoylphenyl)methyl]-10-carbamoyl-5,6,7,8,9,10-hexahydro-cyclohept[b]indol-1-yloxy)-acetic acid,
(5-[(3-carbamoylphenyl)methyl]-10-carbamoyl-5,6,7,8,9,10-hexahydro-cyclohept[b]indol-1-yloxy)-acetic acid,
(5-[(4-carbamoylphenyl)methyl]-10-carbamoyl-5,6,7,8,9,10-hexahydro-cyclohept[b]indol-1-yloxy)-acetic acid,
(5-[(2-methylsulfonylphenyl)methyl]-10-carbamoyl-5,6,7,8,9,10-hexahydro-cyclohept[b]indol-1-yloxy)-acetic acid,
(5-[(3-methylsulfonylphenyl)methyl]-10-carbamoyl-5,6,7,8,9,10-hexahydro-cyclohept[b]indol-1-yloxy)-acetic acid,
(5-[(4-methylsulfonylphenyl)methyl]-10-carbamoyl-5,6,7,8,9,10-hexahydro-cyclohept[b]indol-1-yloxy)-acetic acid,
(5-[(2-methylphenyl)methyl]-10-carbamoyl-5,6,7,8,9,10-hexahydro-cyclohept[b]indol-1-yloxy)-acetic acid,
(5-[(3-methylphenyl)methyl]-10-carbamoyl-5,6,7,8,9,10-hexahydro-cyclohept[b]indol-1-yloxy)-acetic acid,
(5-[(4-methylphenyl)methyl]-10-carbamoyl-5,6,7,8,9,10-hexahydro-cyclohept[b]indol-1-yloxy)-acetic acid,
(5-[(2-ethylphenyl)methyl]-10-carbamoyl-5,6,7,8,9,10-hexahydro-cyclohept[b]indol-1-yloxy)-acetic acid,
(5-[(3-ethylphenyl)methyl]-10-carbamoyl-5,6,7,8,9,10-hexahydro-cyclohept[b]indol-1-yloxy)-acetic acid,
(5-[(4-ethylphenyl)methyl]-10-carbamoyl-5,6,7,8,9,10-hexahydro-cyclohept[b]indol-1-yloxy)-acetic acid,
(5-[(2-trifluoromethylphenyl)methyl]-10-carbamoyl-5,6,7,8,9,10-hexahydro-cyclohept[b]indol-1-yloxy)-acetic acid,
(5-[(3-trifluoromethylphenyl)methyl]-10-carbamoyl-5,6,7,8,9,10-hexahydro-cyclohept[b]indol-1-yloxy)-acetic acid,
(5-[(4-trifluoromethylphenyl)methyl]-10-carbamoyl-5,6,7,8,9,10-hexahydro-cyclohept[b]indol-1-yloxy)-acetic acid,
(5-[(cyclopropylphenyl)methyl]-10-carbamoyl-5,6,7,8,9,10-hexahydro-cyclohept[b]indol-1-yloxy)-acetic acid,
(5-[(cyclobutylphenyl)methyl]-10-carbamoyl-5,6,7,8,9,10-hexahydro-cyclohept[b]indol-1-yloxy)-acetic acid,
(5-[(cyclopentylphenyl)methyl]-10-carbamoyl-5,6,7,8,9,10-hexahydro-cyclohept[b]indol-1-yloxy)-acetic acid,
(5-[(cycloheptylphenyl)methyl]-10-carbamoyl-5,6,7,8,9,10-hexahydro-cyclohept[b]indol-1-yloxy)-acetic acid,
(5-[(2-methoxyphenyl)methyl]-10-carbamoyl-5,6,7,8,9,10-hexahydro-cyclohept[b]indol-1-yloxy)-acetic acid,
(5-[(3-methoxyphenyl)methyl]-10-carbamoyl-5,6,7,8,9,10-hexahydro-cyclohept[b]indol-1-yloxy)-acetic acid,
(5-[(4-methoxyphenyl)methyl]-10-carbamoyl-5,6,7,8,9,10-hexahydro-cyclohept[b]indol-1-yloxy)-acetic acid,
(5-[(2-ethoxyphenyl)methyl]-10-carbamoyl-5,6,7,8,9,10-hexahydro-cyclohept[b]indol-1-yloxy)-acetic acid,
(5-[(3-ethoxyphenyl)methyl]-10-carbamoyl-5,6,7,8,9,10-hexahydro-cyclohept[b]indol-1-yloxy)-acetic acid,
(5-[(4-ethoxyphenyl)methyl]-10-carbamoyl-5,6,7,8,9,10-hexahydro-cyclohept[b]indol-1-yloxy)-acetic acid,
(5-[(2-trifluoromethoxyphenyl)methyl]-10-carbamoyl-5,6,7,8,9,10-hexahydro-cyclohept[b]indol-1-yloxy)-acetic acid,
(5-[(3-trifluoromethoxyphenyl)methyl]-10-carbamoyl-5,6,7,8,9,10-hexahydro-cyclohept[b]indol-1-yloxy)-acetic acid,
(5-[(4-trifluoromethoxyphenyl)methyl]-10-carbamoyl-5,6,7,8,9,10-hexahydro-cyclohept[b]indol-1-yloxy)-acetic acid,
(5-[(2-cyanophenyl)methyl]-10-carbamoyl-5,6,7,8,9,10-hexahydro-cyclohept[b]indol-1-yloxy)-acetic acid,
(5-[(3-cyanophenyl)methyl]-10-carbamoyl-5,6,7,8,9,10-hexahydro-cyclohept[b]indol-1-yloxy)-acetic acid,
(5-[(4-cyanophenyl)methyl]-10-carbamoyl-5,6,7,8,9,10-hexahydro-cyclohept[b]indol-1-yloxy)-acetic acid,
(5-[(2-pyridyl)methyl]-10-carbamoyl-5,6,7,8,9,10-hexahydro-cyclohept[b]indol-1-yloxy)-acetic acid,
(5-[(3-pyridyl)methyl]-10-carbamoyl-5,6,7,8,9,10-hexahydro-cyclohept[b]indol-1-yloxy)-acetic acid,
(5-[(4-pyridyl)methyl]-10-carbamoyl-5,6,7,8,9,10-hexahydro-cyclohept[b]indol-1-yloxy)-acetic acid,
(5-[(2-furyl)methyl]-10-carbamoyl-5,6,7,8,9,10-hexahydro-cyclohept[b]indol-1-yloxy)-acetic acid, (5-[(3-furyl)methyl]-10-carbamoyl-5,6,7,8,9,10-hexahydro-cyclohept[b]indol-1-yloxy)-acetic acid,
(5-[(2-thienyl)methyl]-10-carbamoyl-5,6,7,8,9,10-hexahydro-cyclohept[b]indol-1-yloxy)-acetic acid,
(5-[(3-thienyl)methyl]-10-carbamoyl-5,6,7,8,9,10-hexahydro-cyclohept[b]indol-1-yloxy)-acetic acid,
(5-[(2-benzyl)methyl]-10-carbamoyl-5,6,7,8,9,10-hexahydro-cyclohept[b]indol-1-yloxy)-acetic acid,
(5-[(3-benzyl)methyl]-10-carbamoyl-5,6,7,8,9,10-hexahydro-cyclohept[b]indol-1-yloxy)-acetic acid,
(5-[(4-benzyl)methyl]-10-carbamoyl-5,6,7,8,9,10-hexahydro-cyclohept[b]indol-1-yloxy)-acetic acid,
(5-[(2-phenylphenyl)methyl]-10-carbamoyl-5,6,7,8,9,10-hexahydro-cyclohept[b]indol-1-yloxy)-acetic acid,
(5-[(3-phenylphenyl)methyl]-10-carbamoyl-5,6,7,8,9,10-hexahydro-cyclohept[b]indol-1-yloxy)-acetic acid,
(5-[(4-phenylphenyl)methyl]-10-carbamoyl-5,6,7,8,9,10-hexahydro-cyclohept[b]indol-1-yloxy)-acetic acid,
(5-[(1-napthyl)methyl]-10-carbamoyl-5,6,7,8,9,10-hexahydro-cyclohept[b]indol-1-yloxy)-acetic acid,
(5-[(2-napthyl)methyl]-10-carbamoyl-5,6,7,8,9,10-hexahydro-cyclohept[b]indol-1-yloxy)-acetic acid,
(5-[(2,3-difluorophenyl)methyl]-10-carbamoyl-5,6,7,8,9,10-hexahydro-cyclohept[b]indol-1-yloxy)-acetic acid,
(5-[(2,4-difluorophenyl)methyl]-10-carbamoyl-5,6,7,8,9,10-hexahydro-cyclohept[b]indol-1-yloxy)-acetic acid,
(5-[(2,5-difluorophenyl)methyl]-10-carbamoyl-5,6,7,8,9,10-hexahydro-cyclohept[b]indol-1-yloxy)-acetic acid,
(5-[(2,6-difluorophenyl)methyl]-10-carbamoyl-5,6,7,8,9,10-hexahydro-cyclohept[b]indol-1-yloxy)-acetic acid,
(5-[(3,4-difluorophenyl)methyl]-10-carbamoyl-5,6,7,8,9,10-hexahydro-cyclohept[b]indol-1-yloxy)-acetic acid,
(5-[(3,5-difluorophenyl)methyl]-10-carbamoyl-5,6,7,8,9,10-hexahydro-cyclohept[b]indol-1-yloxy)-acetic acid,
(5-[(3,6-difluorophenyl)methyl]-10-carbamoyl-5,6,7,8,9,10-hexahydro-cyclohept[b]indol-1-yloxy)-acetic acid,
(5-[(2,3-dimethylphenyl)methyl]-10-carbamoyl-5,6,7,8,9,10-hexahydro-cyclohept[b]indol-1-yloxy)-acetic acid,
(5-[(2,4-dimethylphenyl)methyl]-10-carbamoyl-5,6,7,8,9,10-hexahydro-cyclohept[b]indol-1-yloxy)-acetic acid,
(5-[(2,5-dimethylphenyl)methyl]-10-carbamoyl-5,6,7,8,9,10-hexahydro-cyclohept[b]indol-1-yloxy)-acetic acid,
(5-[(2,6-dimethylphenyl)methyl]-10-carbamoyl-5,6,7,8,9,10-hexahydro-cyclohept[b]indol-1-yloxy)-acetic acid,
(5-[(3,4-dimethylphenyl)methyl]-10-carbamoyl-5,6,7,8,9,10-hexahydro-cyclohept[b]indol-1-yloxy)-acetic acid,
(5-[(3,5-dimethylphenyl)methyl]-10-carbamoyl-5,6,7,8,9,10-hexahydro-cyclohept[b]indol-1-yloxy)-acetic acid,
(5-benzyl-10-carbamoyl-5,6,7,8,9,10-hexahydro-cyclohept[b]indol-1-yloxy)-acetic acid, methyl ester,
(5-[(2-phenoxyphenyl)methyl]-10-carbamoyl-5,6,7,8,9,10-hexahydro-cyclohept[b]indol-1-yloxy)-acetic acid, methyl ester,
(5-[(3-phenoxyphenyl)methyl]-10-carbamoyl-5,6,7,8,9,10-hexahydro-cyclohept[b]indol-1-yloxy)-acetic acid, methyl ester,
(5-[(4-phenoxyphenyl)methyl]-10-carbamoyl-5,6,7,8,9,10-hexahydro-cyclohept[b]indol-1-yloxy)-acetic acid, methyl ester,
(5-[(2-fluorophenyl)methyl]-10-carbamoyl-5,6,7,8,9,10-hexahydro-cyclohept[b]indol-1-yloxy)-acetic acid, methyl ester,
(5-[(3-fluorophenyl)methyl]-10-carbamoyl-5,6,7,8,9,10-hexahydro-cyclohept[b]indol-1-yloxy)-acetic acid, methyl ester,
(5-[(4-fluorophenyl)methyl]-10-carbamoyl-5,6,7,8,9,10-hexahydro-cyclohept[b]indol-1-yloxy)-acetic acid, methyl ester,
(5-[(2-chlorophenyl)methyl]-10-carbamoyl-5,6,7,8,9,10-hexahydro-cyclohept[b]indol-1-yloxy)-acetic acid, methyl ester,
(5-[(3-chlorophenyl)methyl]-10-carbamoyl-5,6,7,8,9,10-hexahydro-cyclohept[b]indol-1-yloxy)-acetic acid, methyl ester,
(5-[(4-chlorophenyl)methyl]-10-carbamoyl-5,6,7,8,9,10-hexahydro-cyclohept[b]indol-1-yloxy)-acetic acid, methyl ester,
(5-[(2-bromophenyl)methyl]-10-carbamoyl-5,6,7,8,9,10-hexahydro-cyclohept[b]indol-1-yloxy)-acetic acid, methyl ester,
(5-[(3-bromophenyl)methyl]-10-carbamoyl-5,6,7,8,9,10-hexahydro-cyclohept[b]indol-1-yloxy)-acetic acid, methyl ester,
(5-[(4-bromophenyl)methyl]-10-carbamoyl-5,6,7,8,9,10-hexahydro-cyclohept[b]indol-1-yloxy)-acetic acid, methyl ester,
(5-[(2-iodophenyl)methyl]-10-carbamoyl-5,6,7,8,9,10-hexahydro-cyclohept[b]indol-1-yloxy)-acetic acid, methyl ester,
(5-[(3-iodophenyl)methyl]-10-carbamoyl-5,6,7,8,9,10-hexahydro-cyclohept[b]indol-1-yloxy)-acetic acid, methyl ester,
(5-[(4-iodophenyl)methyl]-10-carbamoyl-5,6,7,8,9,10-hexahydro-cyclohept[b]indol-1-yloxy)-acetic acid, methyl ester,
(5-[(2-acetamidophenyl)methyl]-10-carbamoyl-5,6,7,8,9,10-hexahydro-cyclohept[b]indol-1-yloxy)-acetic acid, methyl ester,
(5-[(3-acetamidophenyl)methyl]-10-carbamoyl-5,6,7,8,9,10-hexahydro-cyclohept[b]indol-1-yloxy)-acetic acid, methyl ester,
(5-[(4-acetamidophenyl)methyl]-10-carbamoyl-5,6,7,8,9,10-hexahydro-cyclohept[b]indol-1-yloxy)-acetic acid, methyl ester,
(5-[(2-carbamoylphenyl)methyl]-10-carbamoyl-5,6,7,8,9,10-hexahydro-cyclohept[b]indol-1-yloxy)-acetic acid, methyl ester,
(5-[(3-carbamoylphenyl)methyl]-10-carbamoyl-5,6,7,8,9,10-hexahydro-cyclohept[b]indol-1-yloxy)-acetic acid, methyl ester,
(5-[(4-carbamoylphenyl)methyl]-10-carbamoyl-5,6,7,8,9,10-hexahydro-cyclohept[b]indol-1-yloxy)-acetic acid, methyl ester,
(5-[(2-methylsulfonylphenyl)methyl]-10-carbamoyl-5,6,7,8,9,10-hexahydro-cyclohept[b]indol-1-yloxy)-acetic acid, methyl ester,
(5-[(3-methylsulfonylphenyl)methyl]-10-carbamoyl-5,6,7,8,9,10-hexahydro-cyclohept[b]indol-1-yloxy)-acetic acid, methyl ester,
(5-[(4-methylsulfonylphenyl)methyl]-10-carbamoyl-5,6,7,8,9,10-hexahydro-cyclohept[b]indol-1-yloxy)-acetic acid, methyl ester,
(5-[(2-methylphenyl)methyl]-10-carbamoyl-5,6,7,8,9,10-hexahydro-cyclohept[b]indol-1-yloxy)-acetic acid, methyl ester,
(5-[(3-methylphenyl)methyl]-10-carbamoyl-5,6,7,8,9,10-hexahydro-cyclohept[b]indol-1-yloxy)-acetic acid, methyl ester,
(5-[(4-methylphenyl)methyl]-10-carbamoyl-5,6,7,8,9,10-hexahydro-cyclohept[b]indol-1-yloxy)-acetic acid, methyl ester, (5-[(2-ethylphenyl)methyl]-10-carbamoyl-5,6,7,8,9,10-hexahydro-cyclohept[b]indol-1-yloxy)-acetic acid, methyl ester,
(5-[(3-ethylphenyl)methyl]-10-carbamoyl-5,6,7,8,9,10-hexahydro-cyclohept[b]indol-1-yloxy)-acetic acid, methyl ester,
(5-[(4-ethylphenyl)methyl]-10-carbamoyl-5,6,7,8,9,10-hexahydro-cyclohept[b]indol-1-yloxy)-acetic acid, methyl ester,
(5-[(2-trifluoromethylphenyl)methyl]-10-carbamoyl-5,6,7,8,9,10-hexahydro-cyclohept[b]indol-1-yloxy)-acetic acid, methyl ester,
(5-[(3-trifluoromethylphenyl)methyl]-10-carbamoyl-5,6,7,8,9,10-hexahydro-cyclohept[b]indol-1-yloxy)-acetic acid, methyl ester,
(5-[(4-trifluoromethylphenyl)methyl]-10-carbamoyl-5,6,7,8,9,10-hexahydro-cyclohept[b]indol-1-yloxy)-acetic acid, methyl ester,
(5-[(cyclopropylphenyl)methyl]-10-carbamoyl-5,6,7,8,9,10-hexahydro-cyclohept[b]indol-1-yloxy)-acetic acid, methyl ester,
(5-[(cyclobutylphenyl)methyl]-10-carbamoyl-5,6,7,8,9,10-hexahydro-cyclohept[b]indol-1-yloxy)-acetic acid, methyl ester,
(5-[(cyclopentylphenyl)methyl]-10-carbamoyl-5,6,7,8,9,10-hexahydro-cyclohept[b]indol-1-yloxy)-acetic acid, methyl ester,
(5-[(cycloheptylphenyl)methyl]-10-carbamoyl-5,6,7,8,9,10-hexahydro-cyclohept[b]indol-1-yloxy)-acetic acid, methyl ester,
(5-[(2-methoxyphenyl)methyl]-10-carbamoyl-5,6,7,8,9,10-hexahydro-cyclohept[b]indol-1-yloxy)-acetic acid, methyl ester,
(5-[(3-methoxyphenyl)methyl]-10-carbamoyl-5,6,7,8,9,10-hexahydro-cyclohept[b]indol-1-yloxy)-acetic acid, methyl ester,
(5-[(4-methoxyphenyl)methyl]-10-carbamoyl-5,6,7,8,9,10-hexahydro-cyclohept[b]indol-1-yloxy)-acetic acid, methyl ester,
(5-[(2-ethoxyphenyl)methyl]-10-carbamoyl-5,6,7,8,9,10-hexahydro-cyclohept[b]indol-1-yloxy)-acetic acid, methyl ester,
(5-[(3-ethoxyphenyl)methyl]-10-carbamoyl-5,6,7,8,9,10-hexahydro-cyclohept[b]indol-1-yloxy)-acetic acid, methyl ester,
(5-[(4-ethoxyphenyl)methyl]-10-carbamoyl-5,6,7,8,9,10-hexahydro-cyclohept[b]indol-1-yloxy)-acetic acid, methyl ester,
(5-[(2-trifluoromethoxyphenyl)methyl]-10-carbamoyl-5,6,7,8,9,10-hexahydro-cyclohept[b]indol-1-yloxy)-acetic acid, methyl ester,
(5-[(3-trifluoromethoxyphenyl)methyl]-10-carbamoyl-5,6,7,8,9,10-hexahydro-cyclohept[b]indol-1-yloxy)-acetic acid, methyl ester,
(5-[(4-trifluoromethoxyphenyl)methyl]-10-carbamoyl-5,6,7,8,9,10-hexahydro-cyclohept[b]indol-1-yloxy)-acetic acid, methyl ester,
(5-[(2-cyanophenyl)methyl]-10-carbamoyl-5,6,7,8,9,10-hexahydro-cyclohept[b]indol-1-yloxy)-acetic acid, methyl ester,
(5-[(3-cyanophenyl)methyl]-10-carbamoyl-5,6,7,8,9,10-hexahydro-cyclohept[b]indol-1-yloxy)-acetic acid, methyl ester,
(5-[(4-cyanophenyl)methyl]-10-carbamoyl-5,6,7,8,9,10-hexahydro-cyclohept[b]indol-1-yloxy)-acetic acid, methyl ester,
(5-[(2-pyridyl)methyl]-10-carbamoyl-5,6,7,8,9,10-hexahydro-cyclohept[b]indol-1-yloxy)-acetic acid, methyl ester,
(5-[(3-pyridyl)methyl]-10-carbamoyl-5,6,7,8,9,10-hexahydro-cyclohept[b]indol-1-yloxy)-acetic acid, methyl ester,
(5-[(4-pyridyl)methyl]-10-carbamoyl-5,6,7,8,9,10-hexahydro-cyclohept[b]indol-1-yloxy)-acetic acid, methyl ester,
(5-[(2-furyl)methyl]-10-carbamoyl-5,6,7,8,9,10-hexahydro-cyclohept[b]indol-1-yloxy)-acetic acid, methyl ester,
(5-[(3-furyl)methyl]-10-carbamoyl-5,6,7,8,9,10-hexahydro-cyclohept[b]indol-1-yloxy)-acetic acid, methyl ester,
(5-[(2-thienyl)methyl]-10-carbamoyl-5,6,7,8,9,10-hexahydro-cyclohept[b]indol-1-yloxy)-acetic acid, methyl ester,
(5-[(3-thienyl)methyl]-10-carbamoyl-5,6,7,8,9,10-hexahydro-cyclohept[b]indol-1-yloxy)-acetic acid, methyl ester,
(5-[(2-benzyl)methyl]-10-carbamoyl-5,6,7,8,9,10-hexahydro-cyclohept[b]indol-1-yloxy)-acetic acid, methyl ester,
(5-[(3-benzyl)methyl]-10-carbamoyl-5,6,7,8,9,10-hexahydro-cyclohept[b]indol-1-yloxy)-acetic acid, methyl ester,
(5-[(4-benzyl)methyl]-10-carbamoyl-5,6,7,8,9,10-hexahydro-cyclohept[b]indol-1-yloxy)-acetic acid, methyl ester,
(5-[(2-phenylphenyl)methyl]-10-carbamoyl-5,6,7,8,9,10-hexahydro-cyclohept[b]indol-1-yloxy)-acetic acid, methyl ester,
(5-[(3-phenylphenyl)methyl]-10-carbamoyl-5,6,7,8,9,10-hexahydro-cyclohept[b]indol-1-yloxy)-acetic acid, methyl ester,
(5-[(4-phenylphenyl)methyl]-10-carbamoyl-5,6,7,8,9,10-hexahydro-cyclohept[b]indol-1-yloxy)-acetic acid, methyl ester,
(5-[(1-napthyl)methyl]-10-carbamoyl-5,6,7,8,9,10-hexahydro-cyclohept[b]indol-1-yloxy)-acetic acid, methyl ester,
(5-[(2-napthyl)methyl]-10-carbamoyl-5,6,7,8,9,10-hexahydro-cyclohept[b]indol-1-yloxy)-acetic acid, methyl ester,
(5-[(2,3-difluorophenyl)methyl]-10-carbamoyl-5,6,7,8,9,10-hexahydro-cyclohept[b]indol-1-yloxy)-acetic acid, methyl ester,
(5-[(2,4-difluorophenyl)methyl]-10-carbamoyl-5,6,7,8,9,10-hexahydro-cyclohept[b]indol-1-yloxy)-acetic acid, methyl ester,
(5-[(2,5-difluorophenyl)methyl]-10-carbamoyl-5,6,7,8,9,10-hexahydro-cyclohept[b]indol-1-yloxy)-acetic acid, methyl ester,
(5-[(2,6-difluorophenyl)methyl]-10-carbamoyl-5,6,7,8,9,10-hexahydro-cyclohept[b]indol-1-yloxy)-acetic acid, methyl ester,
(5-[(3,4-difluorophenyl)methyl]-10-carbamoyl-5,6,7,8,9,10-hexahydro-cyclohept[b]indol-1-yloxy)-acetic acid, methyl ester,
(5-[(3,5-difluorophenyl)methyl]-10-carbamoyl-5,6,7,8,9,10-hexahydro-cyclohept[b]indol-1-yloxy)-acetic acid, methyl ester,
(5-[(3,6-difluorophenyl)methyl]-10-carbamoyl-5,6,7,8,9,10-hexahydro-cyclohept[b]indol-1-yloxy)-acetic acid, methyl ester,
(5-[(2,3-dimethylphenyl)methyl]-10-carbamoyl-5,6,7,8,9,10-hexahydro-cyclohept[b]indol-1-yloxy)-acetic acid, methyl ester,
(5-[(2,4-dimethylphenyl)methyl]-10-carbamoyl-5,6,7,8,9,10-hexahydro-cyclohept[b]indol-1-yloxy)-acetic acid, methyl ester,
(5-[(2,5-dimethylphenyl)methyl]-10-carbamoyl-5,6,7,8,9,10-hexahydro-cyclohept[b]indol-1-yloxy)-acetic acid, methyl ester,
(5-[(2,6-dimethylphenyl)methyl]-10-carbamoyl-5,6,7,8,9,10-hexahydro-cyclohept[b]indol-1-yloxy)-acetic acid, methyl ester,
(5-[(3,4-dimethylphenyl)methyl]-10-carbamoyl-5,6,7,8,9,10-hexahydro-cyclohept[b]indol-1-yloxy)-acetic acid, methyl ester,
(5-[(3,5-dimethylphenyl)methyl]-10-carbamoyl-5,6,7,8,9,10-hexahydro-cyclohept[b]indol-1-yloxy)-acetic acid, methyl ester, (5-[(phenyl)methyl]-10-carbamoyl-5,6,7,8,9,10-hexahydro-cyclohept[b]indol-1-yloxy)-acetic acid, morpholinoethyl ester,
(5-[(cyclohexyl)methyl]-10-carbamoyl-5,6,7,8,9,10-hexahydro-cyclohept[b]indol-1-yloxy)-acetic acid, morpholinoethyl ester,
(5-[(cyclopentyl)methyl]-10-carbamoyl-5,6,7,8,9,10-hexahydro-cyclohept[b]indol-1-yloxy)-acetic acid, morpholinoethyl ester,
(5-[(phenyl)methyl]-10-carbamoyl-5,6,7,8,9,10-hexahydro-cyclohept[b]indol-1-yloxy)-acetic acid, N,N-diethylacetamido ester,
(5-[(cyclohexyl)methyl]-10-carbamoyl-5,6,7,8,9,10-hexahydro-cyclohept[b]indol-1-yloxy)-acetic acid, N,N-diethylacetamido ester, and
(5-[(cyclopentyl)methyl]-10-carbamoyl-5,6,7,8,9,10-hexahydro-cyclohept[b]indol-1-yloxy)-acetic acid, N,N-diethylacetamido ester.

More preferred compounds of the invention are represented by the formulae (C1), (C2), and (C3):

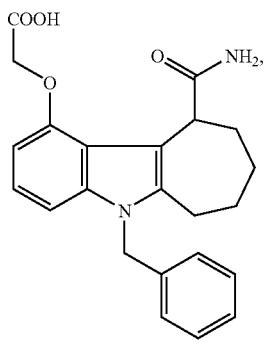

(C1)

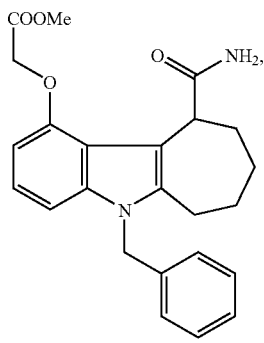

(C2)

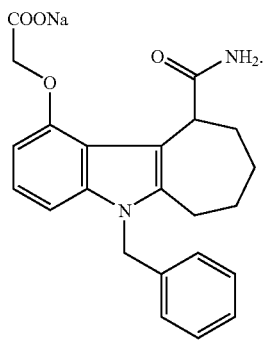

(C3)

The salts of the tricyclic compounds represented by formula (I), are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, chloride, clavulanate, citrate, chloride, edetate, edisylate, estolate, esylate, fluoride, fumarate, glucaptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R— and S— isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities they can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6). Morpholinylethyl ester prodrugs may be prepared by reaction of the sodium salt of a compound of formula (I) (in a medium such as dimethylformamide) with 4-(2-chloroethyl)morpholine hydrochloride (available from Aldrich Chemical Co., Milwaukee, Wis. USA, Item No. C4, 220-3).

III. Method of Preparing the Tricyclic-3-glyoxylamide Compound:

The tricyclic amide compounds are prepared by following a Scheme such as Scheme 1 shown below:

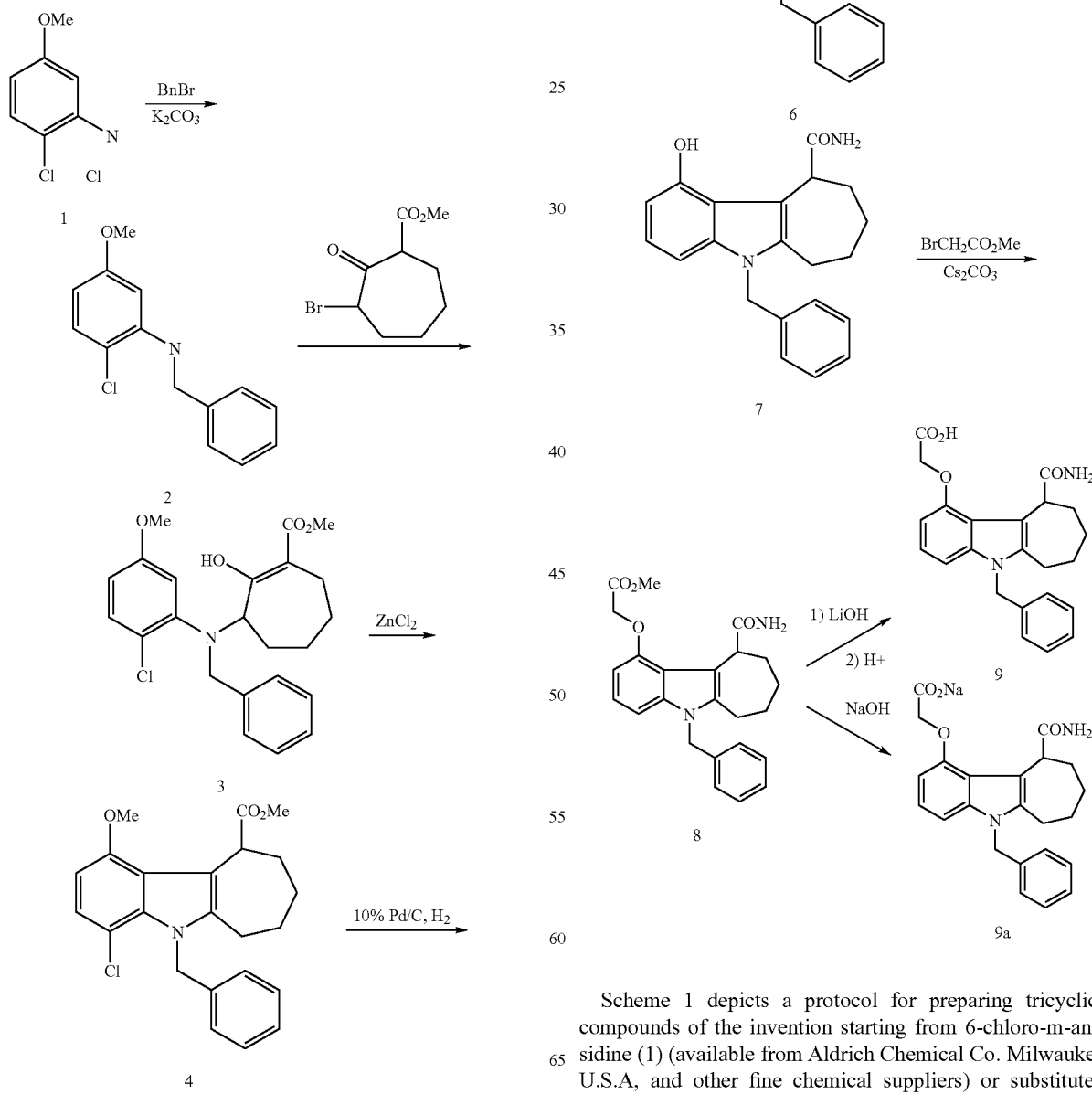

Scheme 1 depicts a protocol for preparing tricyclic-compounds of the invention starting from 6-chloro-m-anisidine (1) (available from Aldrich Chemical Co. Milwaukee U.S.A, and other fine chemical suppliers) or substituted analogs thereof. The starting material (1) may be reductively aminated with benzaldehyde using a mixture of zinc chloride and sodium cyanoborohydride as a reducing agent to form the compound (2). One of skill in the art is aware that the reaction to prepare (2) may be accomplished with other reducing agents including but not limited to $NaBH_4$, HCl/Zn, and $NaCNBH_3$. The choice of aldehyde or ketone to be reductively aminated with compound 1 determines the structure of the group $R_5$ of formula I. For example, the use of formaldehyde in the reductive amination steps would form the N-methyl analog of (2) and ultimately a compound of formula I wherein $R_5$ is methyl. Similarly, the use of cyclohexylacetaldehyde in the reductive amination would ultimately result in a compound of formula I wherein $R_5$ is cyclohexylmethyl.

Alternatively, compound 2 or analog thereof, may be prepared by N-alkylation of a salt of the starting material (1), e.g. hydrochloride salt using an electrophile source and sufficient base to neutralize the acid as well as deprotonate the incipient free amine (i.e. by use of between 2 and 3 mole equivalents of base). For example, in preparing the benzyl analog of 2, compound 1 is reacted with benzyl bromide in the presence of about 3 mole equivalents of a suitable base i.e. potassium carbonate. The reaction is performed in a suitable solvent, preferably dimethylformamide, sufficient to form between about 0.1 to 0.5 molar solution of compound (1). After stirring the reaction mixture at about 10 to 40° C., preferably ambient temperature for about 6 to 48 hours, the reaction mixture is filtered. The filtrate is worked up by dilution of the reaction mixture with organic solvent followed by aqueous extraction. The organic phase is concentrated and the residue chromatographed to obtain desired product as detailed in the experimental section.

A solution of compound (2) is deprotonated at the nitrogen using a base, to form a nucleophile to which is added 2-carbomethoxy-5-bromocycloheptanone. When substitution is desired at positions 1 and/or 3, an appropriately substituted analog of 2-carbomethoxy-5-bromocycloheptanone is employed. The reaction of (2) with 2-carbomethoxy-5-bromocycloheptanone results in a tertiary amine substitution product (compound 3). 2-carbomethoxy-5-bromocycloheptanone and analogs thereof may be prepared by a method similar to that reported by Marx et al. *J. Org. Chem.* 7972, 37, 4489. Strong bases are preferred for de-protonating the benzylamine compound (2). Most preferred is a base selected from potassium(bistrimethylsilyl)amide, lithium diisopropyl amide, and n-butyllithium. After the initial base addition to (2) at about −60 to −10° C., the reaction is preferably performed at ambient temperatures for about 4 to 24 hours. The product (3) is isolated by aqueous work-up and extraction from organic solvents such as, for example, ethyl acetate. The product (3) may be used directly or further purified by chromatography and/or crystallization by methods known to one of skill in the art. Compound (3) dissolved in a suitable solvent e.g. toluene, is heated with zinc chloride at reflux over a period of 10 to 60 hours, preferably about 48 hours, to afford an intermediate tricyclic compound (4) upon purification of the reaction product, for example, by chromatography. Dehalogenation of compound (4) is effected by hydrogenation using Pd/C as catalyst. Preferably, the hydrogenation is performed in a lower boiling alcohol, i.e. methanol, with triethylamine as acid scavenger. While other reducing catalysts may be used, 10% palladium-on-carbon is preferred. The catalyst is also preferably wetted with a protic lower boiling alcohol before use. The product (5) is obtained by filtration over an adsorbent, i.e. silica gel or celite. The product (5) may be further purified by aqueous and/or chromatographic separation techniques.

The compound (5) is de-methylated by reaction with boron tribromide or sodium thioethoxide in a suitable solvent such as dichloromethane. About 1.0 to 12.0 equivalents of boron tribromide is typically sufficient to effect complete de-methylation. The de-methylation reaction temperature is from about −12° C. to about 10° C. Work-up is initiated by stirring with methyl alcohol or other suitable protic solvent. After stirring in methyl alcohol the mixture is neutralized with a base such as sodium bicarbonate. Neutralization is followed by extraction and purification of the organic phase by methods known to one of skill in the art.

The product (6) is ammoniated by a process involving displacement of the methylester by use of excess ammonia in the form of ammonium hydroxide to form the amide functional group at position (10) by nucleophilic substitution. Other methods for the conversion of esters to amides are known to one of skill in the art and may be found in general reference texts (see J. March, *Advanced Organic Chemistry*, 3$^{rd}$ ed., Wiley Interscience Publishers, New York, N.Y., 1985). The product (7) is then dissolved in a suitable solvent e.g. N,N-dimethylformamide, followed by addition of a slight excess (about 1.05 mole equiv. based on (5)) of TRITON-B™ (Aldrich Chemical Co., Milwaukee, USA), cesium carbonate or other mild base, and methyl bromoacetate. The mixture is stirred at ambient temperature to afford compound (8) after about 1 to 6 hours of reaction. Compound (8) is isolated for example, by aqueous wash followed by chromatography of the organic phase. Other 2-substituted haloacetates i.e. benzyl bromoacetate may be used to prepare for example, the benzyl analog of (8).

The free acid (9) is obtained by acidifying the saponification product of (8) or other basification reaction product resulting from hydrolysis, e.g. with potassium or lithium hydroxide. Most inorganic acids are typically suitable for acidification as described previously. However, the use of dilute HCl is preferred. The free acid (9) may be extracted into an organic phase if soluble, and dried by common laboratory methods or dried by removing water from the aqueous phase. Alternatively the saponification reaction (sodium hydroxide reaction with (8)) product (9a), itself a compound of the invention, may be isolated.

Compounds of formula I wherein for $R_{10}$, n is 1, or 2 may be prepared following a protocol such as Scheme 2, 3, or 4 below, or a variation thereof.

Scheme 2

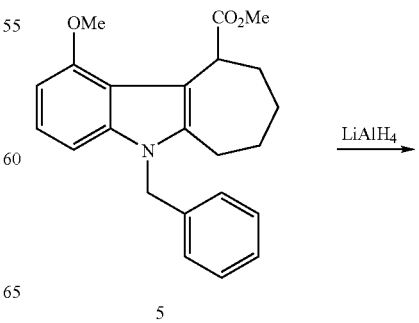

5

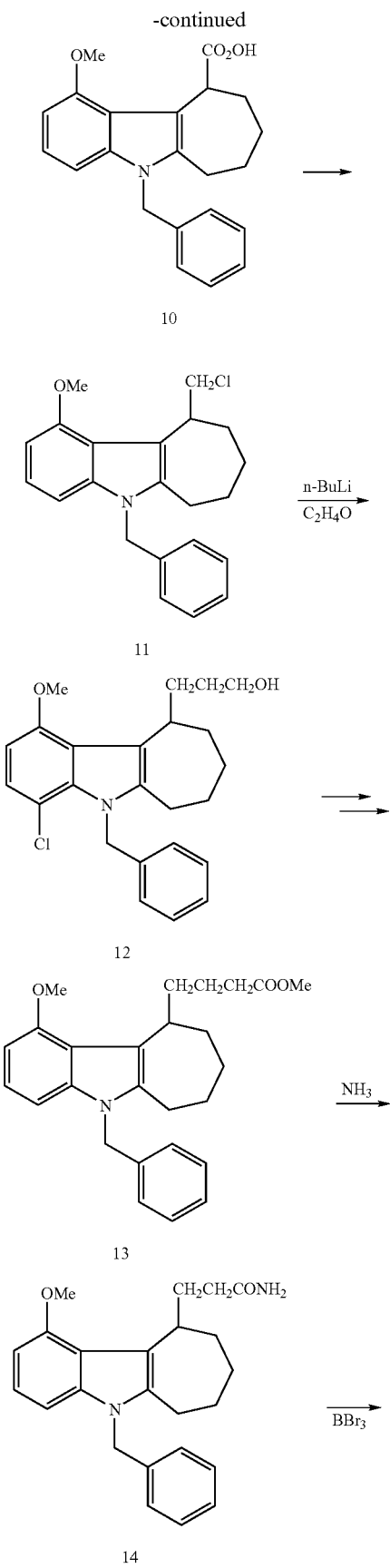

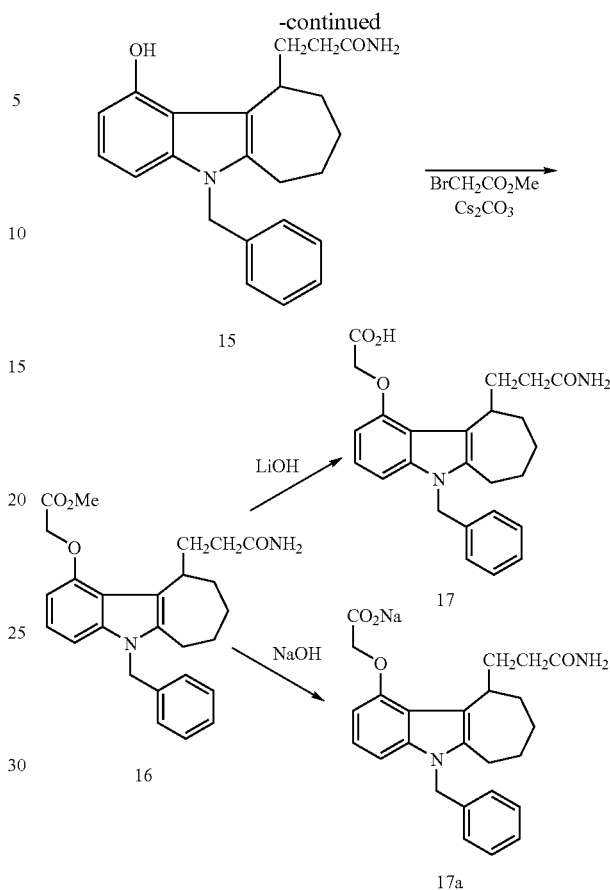

For compounds of formula I, wherein for $R_{10}$, wherein n is 2, i.e. the propanamide, the methyl ester compound (4) may be reduced to the corresponding alcohol. Alternatively, and preferably, the compound (5) from Scheme 1 may be reduced directly to compound (10). The resulting alcohol (10) may be converted to the halide, preferably the chloride (11) or bromide. The halogenation of the alcohol (10) may be accomplished by use of a halogenating agent, i.e. thionyl chloride, or other methods known to one of skill in the art. The halide (11) may be activated by halogen-metal exchange reaction using for example, n-butyllithium. The activated (organolithium) intermediate is then reacted with ethylene oxide, for example, to afford the terminal alcohol compound (12) as shown in Scheme 2.

Conversion of the alcohol (12) to an ester via an intermediate acid may be accomplished, for example, by oxidation of the alcohol (12) with sodium hypochlorite in buffered t-butanol followed by esterification of the incipient acid to the ester (13). Methods for acid to ester conversions are known to one of skill in the art and may be found in general reference texts that have been discussed previously. The ester (13) is then converted to the corresponding amide (14) by use of excess aqueous ammonia. The ester derivative of (13) may also be converted to the corresponding amide derivative (14) or other substituted amide compound by reaction of the ester derivative of (13) with methylchloroaluminum amide in benzene or other suitable solvent or solvent mixtures. (See Levin, J. I.; Turos, E.; Weinreb, S. M. *An alternative procedure for the aluminum-mediated conversion of esters to amides* Syn. Comm., 1982, 12, 989–993). The amide (14) is then de-protected at the 1-position by the use of boron tribromide as described previously, to afford compound (15). The conversion of compound (15) to the oxyacetic acid ester (16), oxyacetic acid (17) or sodium salt (17a) is accomplished as described previously for Scheme 1.

Scheme 3 below illustrates an alternate and preferable Scheme for preparing compounds of formula I wherein for $R_{10}$, n is 2, i.e. the propanamide compound:

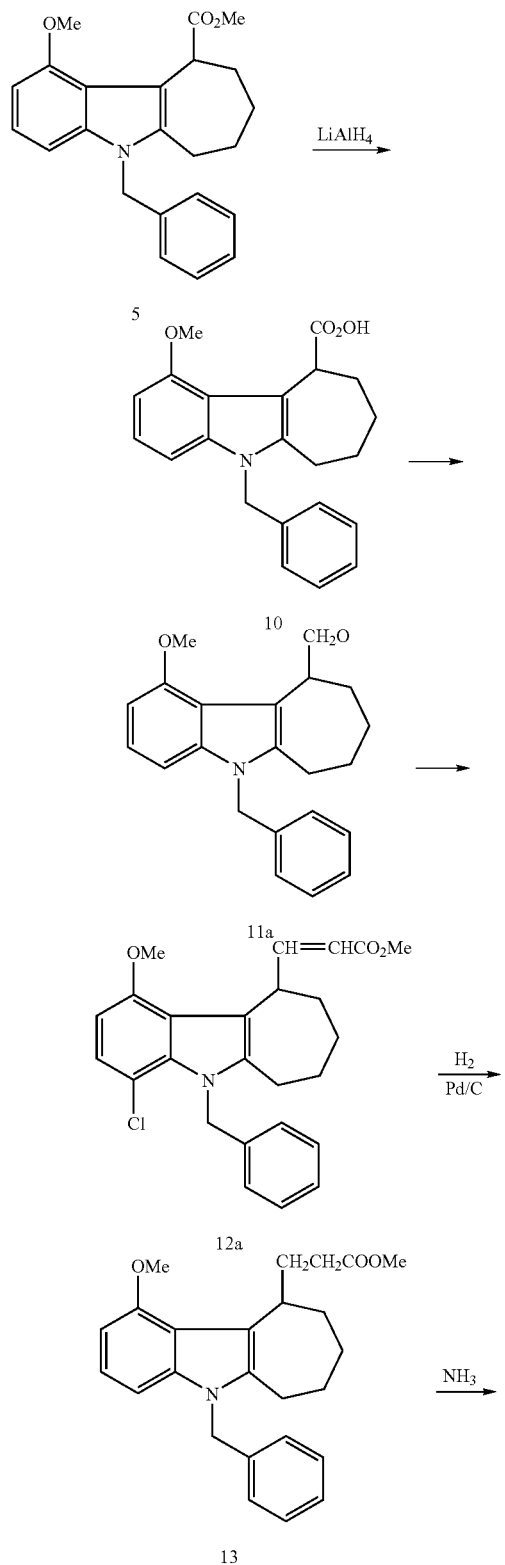

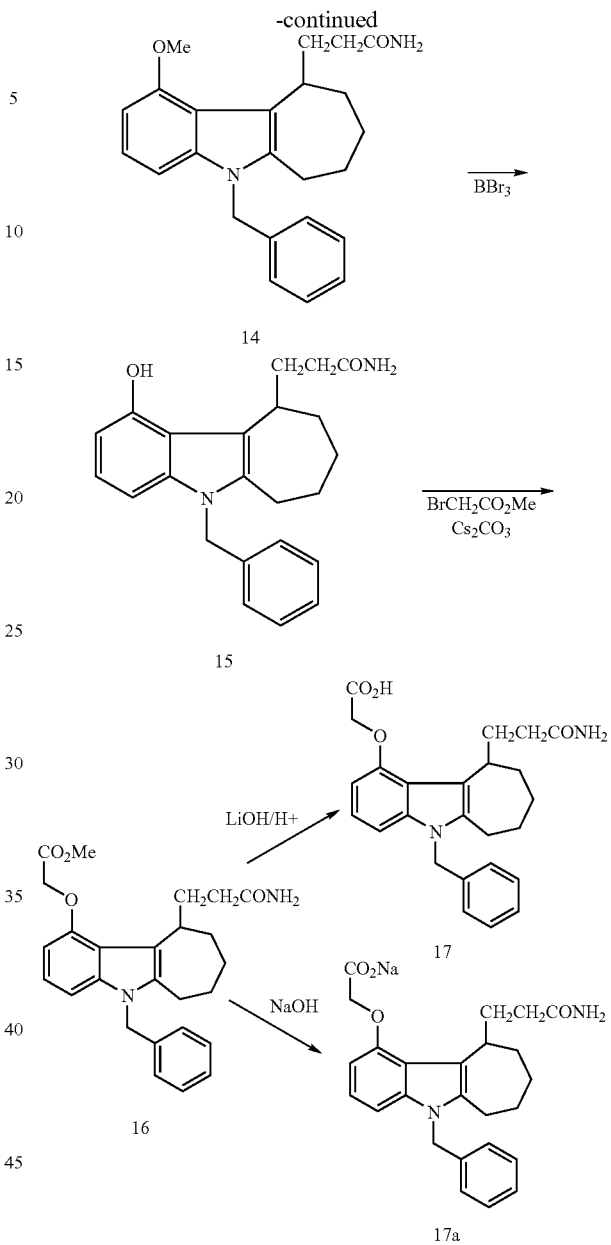

According to Scheme 3, ester (5) is reduced to alcohol (10) as described for Scheme (2). The alcohol (10) is then oxidized to the aldehyde (11a). Oxidation of alcohol (10) to the aldehyde (11a) may be accomplished for example, by the use of sodium hypochlorite in buffered t-butanol, or the use of pyridinium sulfur trioxide complex with diisopropylethylamine as base in dimethyl sulfoxide solvent (see *Tetrahedron Letters,* 28, 1603 (1987)). The aldehyde (11a) is then subjected to a Horner-Emmons modification of the Wittig reaction to afford the α,β-unsaturated ester (12a). Preferably, a reagent for forming the α,β-unsaturated methyl ester (i.e. trimethylphosphonoacetate) is used to react with the aldehyde (11a) in the presence of a base. Preferred bases for the Horner-Emmons reactions include n-butyllithium, sodium hydride and sodium ethoxide. The E-regioisomer of α,β-unsaturated methyl ester or a preponderance of the E regioisomer may be obtained. A general review of Wittig and modified Wittig reactions is provided in *Chem. Rev.,* 89 863 (1989). The ester (12a) may then be reduced using, for example, hydrogenation techniques such as, use of hydrogen with palladium-on-carbon catalysts to afford the reduced ester (13). The ester (13) is converted to the desired oxyacetic ester derivative (17) or (17a) as discussed previously and as shown in Scheme 3.

Compounds of formula I wherein for $R_{10}$, n is 1, i.e. the acetamide derivative, may be prepared as shown in Scheme 4 below:

For example, the halide (11) prepared according to Scheme (2) may be cyanated using sodium cyanide to afford the cyano compound (12b). The cyano compound (12b) may be hydrolyzed to afford the amide compound (14). A preferred procedure for the conversion of (12b) to (14) is the use of a hydrogen peroxide/potassium carbonate mixture in dimethyl sulfoxide solvent. The reaction is typically performed at ambient temperatures and the product is worked up by acidic aqueous quench followed by extraction. The amide (14) is converted to compounds (17) or (17a) as discussed previously. Other procedures for the conversion of the cyano group to the amide group may be found in previously disclosed general reference texts. To prepare compound of formula (I) wherein $R_5$ is a halo-substituted group, i.e. $R_5$ is halosubstituted benzyl or $(C_1-C_{20})$haloalkyl wherein the halo group is chloro, bromo, fluoro or iodo, the process as shown in Scheme 5 below may be utilized.

Scheme 5

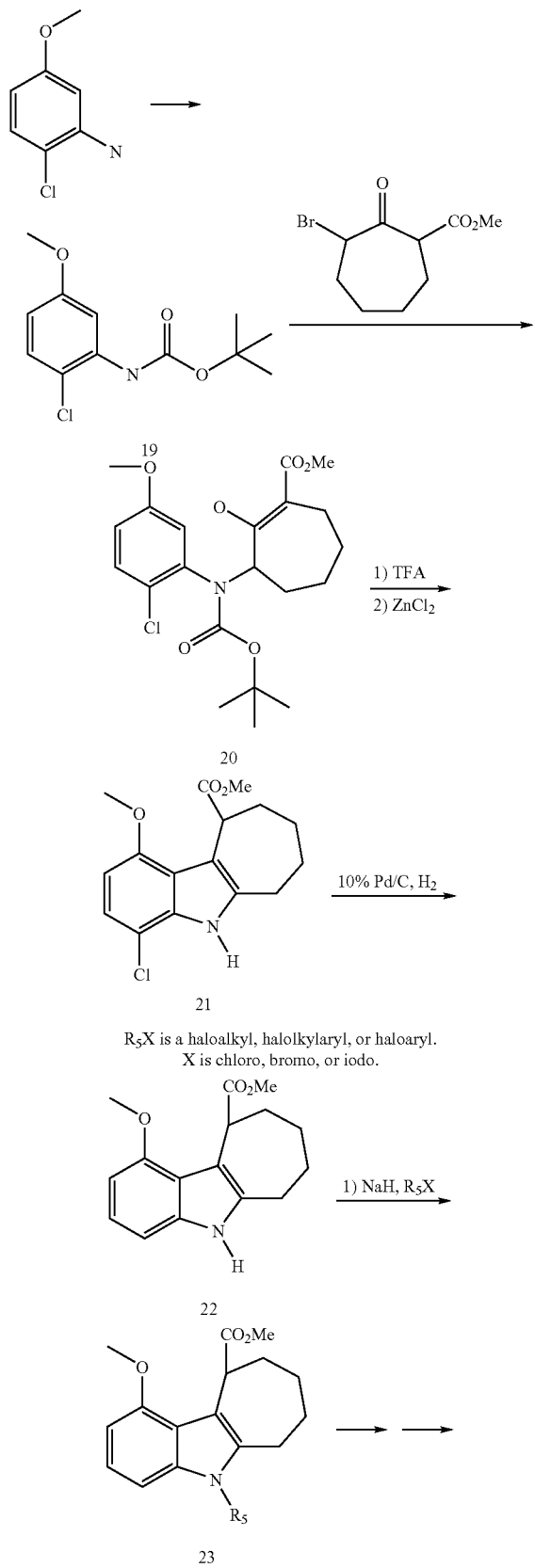

R₅X is a haloalkyl, halolkylaryl, or haloaryl.
X is chloro, bromo, or iodo.

Scheme 5 in addition to its utility in preparing compounds of formula I also provides the advantage of allowing alkylation of the tricyclic nitrogen (5- position of tricyclic nucleus) with haloalkyl, haloalkylaryl or haloalryl groups after formation of the tricycle to avoid dehalogenation of such groups as may obtain following the procedure of Scheme 1. According to Scheme 5, the 6-chloro-m-anisidine is BOC-protected using t-butyloxycarbonyl anhydride (BOC anhydride) (aldrich Chemical Company, Milaukee, USA) or other protecting group to form compound (19). Compound (19) is then substituted at the nitrogen atom with 2-carbomethoxy-5-bromocycloheptanone to form compound (20) using a base as described for Scheme 1. The product (20) is deprotected with trifluoroacetic acid in a suitable solvent to afford an intermediate compound which is then reductively cyclized using zinc chloride in a suitable solvent e.g. toluene at reflux to form compound (21). Compound (21) is dehalogenated using 10% palladium-on-carbon to afford compound (22) in a procedure similar to the procedure of Scheme 1. The dehalogenated product (22) is then arylated or alkylated at the tricyclic nitrogen using a suitable base (in the absence, or presence, of a catalyst) and an appropriately halo-substituted arylhalide or alkylhalide. Arylation of amines can be accomplished by a wide variety of known methods and catalysts and are known to one of skill in the art and may be found in general reference texts (see March's Advanced Organic Chemistry, 5th ed., Wiley Interscience Publishers, New York, N.Y., 2001, page 501–502), for example, according to the general procedures of Watanabe, M.; Nishiyama, M.; Yamamoto, T.; Koie, Y.; *Tetrahedron Lett* 2000, 41 (4), 481–483; Wolfe, J. P.; Buchwald, S. L.; *J. Org. Chem.* 1996, 61, 1133; Morita, S.; Kitano, K.; Matsubara, J.; Ohtani, T.; Kawano, Y.; Otsubo, K.; Uchida, M.; *Tetrahedron [TETRAB]* 1998, 54 (19), 4811–4818; Smith W. J., Sawyer J. S., *Tetrahedron Lett* 37(3), 299–302 (1996); and related references. The resulting haloaryl or haloalkyl compound (23) is subjected to procedures similar to that shown in Scheme 1 (i.e compound 4, Scheme 1) to afford the halosubstituted compound (24).

IV. Methods of Using the Compounds of the Invention:

The tricyclic compounds described herein are believed to achieve their beneficial therapeutic action principally by direct inhibition of mammalian (including human) sPLA₂, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA₂ mediated release of fatty acids comprises contacting mammalian sPLA₂ with a therapeutically effective amount of a tricyclic compound of Formula (I) as described herein including a combination thereof, a salt or a prodrug derivative thereof.

Another aspect of this invention relates to a method for treating inflammatory diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of a tricyclic compound of the invention.

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effect will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention per Formula (I) or pharmaceutical formulations containing these compounds are in unit dosage form for administration to a mammal. The unit dosage form can be a capsule or tablet itself, or the appropriate number of any of these. The quantity of Active Ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the tricyclic compound of the invention together with a pharmaceutically acceptable carrier or diluent therefor. The present pharmaceutical formulations are prepared by known procedures using well-known and readily available ingredients.

In making the compositions of the present invention, the Active Ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid which is in admixture with the finely divided Active Ingredient. In tablets the Active Ingredient is mixed with a carrier having the necessary binding properties in suitable proportions and compacted in the shape and size desired. The powders and tablets preferably contain from about 1 to about 99 weight percent of the Active Ingredient which is the novel compound of this invention. Suitable solid carriers are magnesium carbonate, magnesium stearate, talc, sugar lactose, pectin, dextrin, starch, gelatin, tragacanth, methylcellulose, sodium carboxymethyl cellulose, low melting waxes, and cocoa butter.

Sterile liquid form formulations include suspensions, emulsions, syrups and elixirs.

The Active Ingredient can be dissolved or suspended in a pharmaceutically acceptable carrier, such as sterile water, sterile organic solvent or a mixture of both. The Active Ingredient can often be dissolved in a suitable organic solvent, for instance aqueous propylene glycol. Other compositions can be made by dispersing the finely divided Active Ingredient in aqueous starch or sodium carboxymethyl cellulose solution or in a suitable oil.

The following pharmaceutical formulations 1 through 8 are illustrative only and are not intended to limit the scope of the invention in any way. "Active Ingredient", refers to a compound according to Formula (I) or a pharmaceutically acceptable salt, solvate, racemate or enantiomer thereof.

Formulation 1

Hard gelatin capsules are prepared using the following ingredients:

|   | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

|   | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active Ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active Ingredient, are made as follows:

| Active Ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

| Active Ingredient | 225 mg |
| --- | --- |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 ml dose, are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active Ingredient | 100 mg |
| --- | --- |
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
Reaction Buffer—

| | | |
|---|---|---|
| $CaCl_2 \cdot 2H_2O$ | (1.47 g/L) | |
| KCl | (7.455 g/L) | |
| Bovine Serum Albumin (fatty acid free) (Sigma A-7030, product of Sigma Chemical Co., St. Louis MO, USA) | (1 g/L) | |
| TRIS HCl | (3.94 g/L) | |
| pH 7.5 (adjust with NaOH) | | |

Enzyme Buffer—

| | | |
|---|---|---|
| 0.05 | $NaOAc \cdot 3H_2O$, pH 4.5 | |
| 0.2 | NaCl | |

Adjust pH to 4.5 with acetic acid
DTNB–5,5'-dithiobis-2-nitrobenzoic acid
Racemic Diheptanoyl Thio—PC
racemic 1,2-bis(heptanoylthio)-1,2-dideoxy-sn-glycero-3-phosphorylcholine
Triton X-100™ prepare at 6.249 mg/ml in reaction buffer to equal 10 uM.
Reaction Mixture—
A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of sPLA₂ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

Results

| Compound of Example# | $IC_{50}$ (μM) (micromolar) |
|---|---|
| 1 | 0.248 |

While the present invention has been illustrated above by certain specific embodiments, it is not intended that these specific examples should limit the scope of the invention as described in the appended claims.

Experimental

All of the products of the Examples described below as well as intermediates used in the following procedures showed satisfactory NMR and IR spectra. They also had the correct mass spectral values.

EXAMPLE 1

Preparation of (5-Benzyl-10-carbamoyl-5,6,7,8,9,10-hexahydro-cyclohepta[b]indol-1-yloxy)acetic Acid

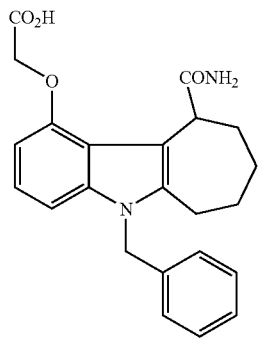

Part A. N-Benzyl-2-chloro-5-methoxyaniline

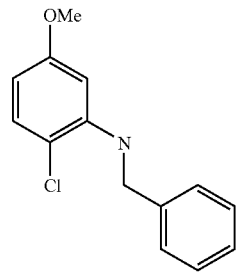

Procedure A:
A solution of 6-chloro-m-anisidine (9.80 g; 62.2 mmol), benzaldehyde (7.60 mL; 74.62 mmol) and $ZnCl_2$ (10.20 g; 74.62 mmol) in 200 mL of MeOH was treated $NaCNBH_3$ (4.70 g; 74.62 mmol) in 0.5 g portions. The reaction was heated to reflux for 2 hr, allowed to cool and additional $NaCNBH_3$ (1.95 g; 31.03 mmol) added. The mixture was stirred at ambient temperature for 72 hrs, poured into aqueous 1 N NaOH (400 mL), and extracted multiple times with $Et_2O$ (1 L total). The combined organic layers were dried ($Na_2SO_4$), filtered, and concentrated in vacuo. The black solid was purified by MPLC (1.25% EtOAc in hexanes) to afford the title compound as an oil (8.46 g; 32.89 mmol; 55%). ¹H NMR (CDCl₃) δ 7.44–7.27 (m, 5H), 7.20–7.14 (m, 1H), 6.26–6.18 (m, 2H), 4.72 (br s, 1H), 4.38 (d, J=5.6 Hz, 2H), 3.71 (s, 3H); IR (CHCl$_3$) 1604, 1583, 1513, 1466, 1453, 1318, 1173, 1027 cm$^{-1}$; FDMS 248 (M+1); Anal. calcd for C$_{14}$H$_{14}$NOCl: C, 67.88; H, 5.70; N, 5.65. Found: C, 68.05; H, 5.64; N, 5.72.

Procedure B:

A slurry of 6-chloro-m-anisidine hydrochloride (25 g; 128.8 mmol), benzylbromide (15 mL; 128.8 mmol) and K$_2$CO$_3$ (53.4 g; 386.4 mmol) in 500 mL of DMF was allowed to stir at ambient temperature for 3 d. The reaction mixture was filtered over a pad of celite to remove solid K$_2$CO$_3$. EtOAc and water (500 mL each) were added to the filtrate. The resulting organic layer was washed with water (3×500 mL), adding just enough brine to break the resulting emulsions. The original aqueous layer was extracted with EtOAc (200 mL), and the combined organic layers were dried over Na$_2$SO$_4$ and concentrated in vacuo. The black oily residue was purified by flash chromatography (5% EtOAc in hexanes) followed by trituration with Et$_2$O and hexanes to give a white crystalline solid (17.5 g; 70.6 mmol; 55%). FDMS 247 (M+)

Part B. 2–Carbomethoxy-5-Bromocycloheptanone

In a method similar to that reported in Marx et al. *J. Org. Chem.* 1972, 37, 4489, a solution of methyl 2-oxo-1-cycloheptanone carboxylate (10.9 g; 64 mmol) in CHCl$_3$ at 0° C. was treated with bromine (3.3 mL, 64 mmol) dropwise. After stirring 2 h at 0° C. and sitting overnight in the freezer, the reaction mixture was concentrated in vacuo. The residual oil was dissolved in 250 mL of CH$_2$Cl$_2$. The organic solution was washed with H$_2$O (2×250 mL) and saturated NaHCO$_3$ solution (250 mL), dried over Na$_2$SO$_4$ and concentrated in vacuo. The residual oil was distilled under vacuum (0.1 mmHg; 150° C.) to give 14.46 g (58 mmol; 91%) of the title, compound. ES-MS: 249, 251 (M+1)$^+$; Anal calcd for C$_9$H$_{13}$O$_3$Br: C, 43.39; H, 5.26. Found: C, 45.94; H, 5.72.

Part C. 5-Benzyl-4-chloro-1-methoxy-5,6,7,8,9,10-hexahydro-cyclohepta[b]indole-10-carboxylic Acid Methyl Ester

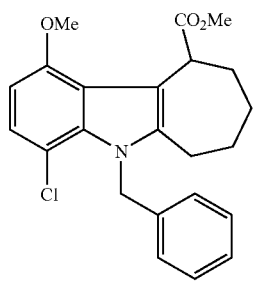

A solution of N-benzyl-2-chloro-5-methoxyaniline (15.9 g; 64.2 mmol) in 300 mL of THF, cooled to about 0° C., was treated with potassium bis(trimethylsilyl)amide (0.5 M in toluene; 270 mL; 134.8 mmol) in a dropwise manner. After stirring 30 min at 0° C., a solution of 2-carbomethoxy-5-bromocycloheptanone (Part B; 17.6 g; 70.6 mmol) in 65 mL THF was added dropwise. The reaction was stirred overnight at ambient temperature and was quenched with aqueous NH$_4$Cl (500 mL). The two layers were separated, and the aqueous phase was extracted twice with EtOAc. The combined organic layers were washed with brine, dried over Na$_2$SO$_4$, and concentrated in vacuo. Purification by flash chromatography (gradient of 0% to 5% to 10% EtOAc in hexanes) afforded 17.1 g (41.1 mmol; 64%) of the intermediate uncyclized enol [ES-MS: 416 (M+1)$^+$]. This intermediate was then dissolved in 200 mL of toluene, treated with 1M ZnCl$_2$ in Et$_2$O (165 mL; 164 mmol) and heated at 65° C. (reflux conditions). After 1 h, a white precipitate had formed. An additional 300 mL of toluene and 165 mL of 1M ZnCl$_2$ in Et$_2$O was added, and the reaction mixture was allowed to continue heating for 3 d. The mixture was cooled and filtered. The organic filtrate was washed with water (250 mL), dried over Na$_2$SO$_4$ and concentrated in vacuo. Chromatography on the Waters Prep500 (SiO$_2$ cartridges, gradient of 0% to 5% EtOAc in hexanes) gave 9.37 g (23.5 mmol; 58%) of the title cyclized product as a yellow foam. ES-MS: 398 (M+1)$^+$; Anal calcd for C$_{23}$H$_{24}$NO$_3$Cl: C, 69.43; H, 6.08; N, 3.52. Found: C, 69.56; H, 6.11; N, 3.63.

Part D. 5-Benzyl-1-methoxy-5,6,7,8,9,10-hexahydro-cyclohepta[b]indole-10-carboxylic Acid Methyl Ester

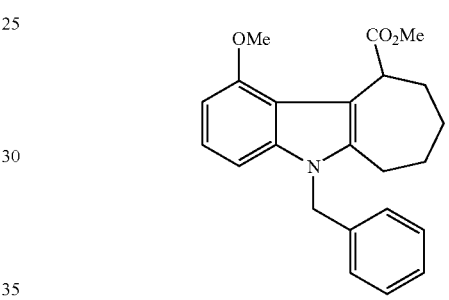

A solution of the tricyclic product from above (4.3 g; 10.8 mmol) in 5 mL of TEA, 50 mL of MeOH and 50 mL of THF was treated with 10% Pd—C (500 mg) which had been pre-wetted with MeOH. The mixture was hydrogenated at atmospheric pressure for 16 hrs. The catalyst was filtered, and the mother liquor was concentrated in vacuo. The crude residue was purified by flash chromatography (5% step gradient of 0% to 15% EtOAc in hexanes) to afford 2.2 g; 6.05 mmol; 56%) of the title compound. ES-MS: 364 (M+1)$^+$; Anal calcd for C$_{23}$H$_{25}$NO$_3$: C, 76.01; H, 6.93; N, 3.85. Found: C, 76.01; H, 7.00; N, 3.81.

Part E. 5-Benzyl-1-hydroxy-5,6,7,8,9,10-hexahydro-cyclohepta[b]indole-10-carboxylic Acid Methyl Ester

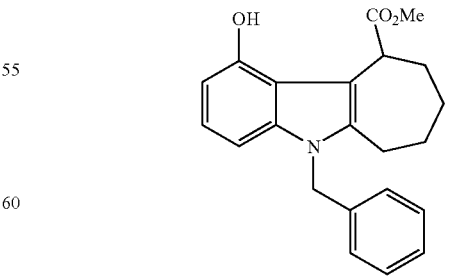

A −10° C. solution of 5-benzyl-1-methoxy-5,6,7,8,9,10-hexahydrocyclohepta[b]-indole-10-carboxylic acid methyl ester (Part D; 2.1 g; 5.78 mmol) in 25 mL of CH$_2$Cl$_2$ was treated dropwise with neat BBr$_3$ (1.1 mL; 11.6 mmol). After 2.5 h, the reaction was quenched with MeOH, warmed to ambient temperature and stirred for an additional 2 h. The reaction mixture was poured into brine (50 mL). Water (50 mL) was added, the layers were separated, and the aqueous layer was extracted with CHCl$_3$ (3×50 mL). The combined organic layers were dried over Na$_2$SO$_4$ and concentrated in vacuo to a dark oil. Purification by flash chromatography (10% step gradient of 10% to 50% EtOAc in hexanes) gave 743 mg (2.13 mmol; 37%) of the title hydroxy compound. ES-MS: 350 (M+1)$^+$; Anal calcd for C$_{22}$H$_{23}$NO$_3$: C, 75.62; H, 6.63; N, 4.01. Found: C, 75.42; H, 6.61; N, 3.91.

Part F. 5-Benzyl-1-hydroxy-5,6,7,8,9,10-hexahydro-cyclohepta[b]indole-10-carboxylic Acid Amide

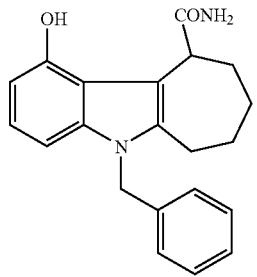

Ammonia gas (ca. 10 mL) was condensed into a −78° C. solution of the methyl ester from Part E (700 mg; 2.0 mmol) in 10 mL of THF in a pressure tube. The tube was then sealed and allowed to stand at ambient temperature for 2d, followed by heating at 50° C. for 1d. The reaction was cooled, and concentrated. The crude residue was triturated with CH$_2$Cl$_2$ to give 321 mg of a tan powder (0.96 mmol; 46%) that was used without further purification. ES-MS: 335 (M+1)$^+$; Anal calcd for C$_{21}$H$_{22}$N$_2$O$_2$.0.1H$_2$O: C, 75.02; H, 6.66; N, 8.33. Found: C, 74.85; H, 6.71; N, 8.11.

Part G. (5-Benzyl-10-carbamoyl-5,6,7,8,9,10-hexahydro-cyclohepta[b]indol-1-yloxy)acetic Acid Methyl Ester

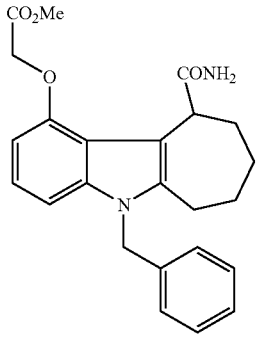

A slurry of 5-benzyl-1-hydroxy-5,6,7,8,9,10-hexahydro-cyclohepta[b]indole-10-carboxylic acid amide (Part F; 275 mg; 0.822 mmol) and Cs$_2$CO$_3$ (670 mg; 2.06 mmol) in 8 mL of DMF was treated with methyl bromoacetate (0.100 mL; 1.07 mmol). After stirring overnight at ambient temperature, the reaction mixture was poured into water and EtOAc (20 mL each). The layers were separated, and the organic phase was washed with water (3×20 mL), dried over Na$_2$SO$_4$ and concentrated in vacuo. Purification by radial chromatography (CHCl$_3$) afforded 205 mg (0.504 mmol; 61%) of the title ester as a white foam. ES-MS: 407 (M+1)$^+$.

Part H. (5-Benzyl-10-carbamoyl-5,6,7,8,9,10-hexahydro-cyclohepta[b]indol-1-yloxy)acetic Acid A slurry of the methyl ester from Part G (60 mg; 0.148 mmol) in 0.3 mL of THF and 0.9 mL of MeOH was treated with 1N aqueous LiOH (0.3 mL). The mixture was stirred for 2 h, then acidified with 0.2 N HCl. The resulting precipitate was filtered and dried in vacuo to give 43 mg (0.11 mmol; 74%) of the title acid as a white solid ES-MS: 393 (M+1)$^+$; Anal calcd for C$_{23}$H$_{24}$N$_2$O$_4$.0.7H$_2$O: C, 68.20; H, 6.32; N, 6.92. Found: C, 68.32; H, 6.22; N, 6.77.

We claim:

1. A tricyclic compound represented by the formula (I), or a pharmaceutically acceptable salt, solvate or prodrug thereof;

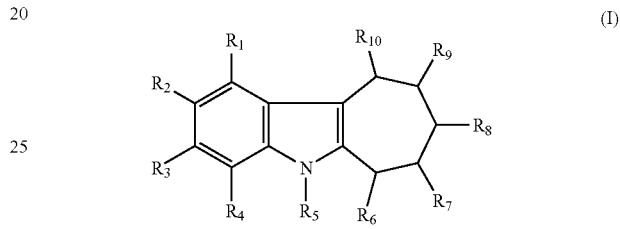

wherein;

R$_1$ is the group —(La)-(acidic group) wherein —(L$_a$)—, is an acid linker having an acid linker length of 1 to 8;

R$_2$, R$_3$, and R$_4$ are each independently selected from non-interfering substituents including hydrogen:

R$_5$ is the group (C$_1$–C$_{20}$)alkyl, (C$_1$–C$_{20}$)haloalkyl, (C$_2$–C$_{20}$)alkenyl, (C$_2$–C$_{20}$)alkynyl, (C$_1$–C$_{10}$)alkylaryl, (C$_1$–C$_5$)alkylcyclohexyl, (C$_1$–C$_5$)alkylcyclopentyl, (C$_1$–C$_5$)alkylcycloheptyl, phenyl, benzyl, methylnaphthyl, (C$_1$–C$_5$)alkylheterocyclic, carbocyclic radical, or heterocyclic radical, or aryl;

R$_6$, R$_7$, R$_8$, and R$_9$, are each independently selected from hydrogen, or a group consisting of 1 to 10 non-hydrogen atoms plus any required hydrogen atoms;

R$_{10}$ is selected from an amide or thioamide group represented by the formula,

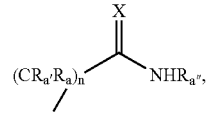

wherein X is oxygen or sulfur, R$_a$ and R$_{a'}$ is independently selected from hydrogen, (C$_1$–C$_8$)alkyl, or aryl; R$_{a''}$ is hydrogen, NH$_2$, (C$_1$–C$_8$)alkyl, aryl, (C$_1$–C$_8$)alkylaryl, or arylalkyl; and n is 0, 1, or 2.

2. The compound of claim 1 wherein R$_6$, is hydrogen, (C$_1$–C$_4$)alkyl, (C$_2$–C$_4$)alkenyl, —O—(C$_1$–C$_3$ alkyl), —S—(C$_1$–C$_3$ alkyl), (C$_3$–C$_4$)cycloalkyl, —CF$_3$, halo, —NO$_2$, —CN, or —SO$_3$.

3. Compound of claim 1 wherein R$_6$, R$_7$, R$_8$, R$_9$ and R$_2$ are independently selected from (C$_1$–C$_4$)alkyl, (C$_2$–C$_4$)alkenyl, —O—(C$_1$–C$_3$ alkyl), —S—(C$_1$–C$_3$ alkyl), (C$_3$–C$_4$) cycloalkyl, —CF$_3$, or halo.

4. The compound of claim 1 wherein for R$_{10}$, the groups R$_a$ or R$_{a'}$ are hydrogen and n is 0, or 1.

5. The compound of claim 1 wherein $R_{10}$ is the group represented by the formula;

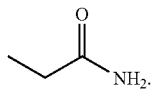

6. The compound of claim 1 wherein $R_{10}$ is the group represented by the formula;

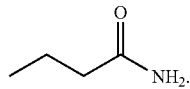

7. The compound of claim 1 wherein $R_{10}$ is the group represented by the formula;

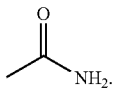

8. The compound of claim 1 wherein, for $R_2$ or $R_3$, or $R_4$ the non-interfering substituent is independently selected from hydrogen, $(C_1-C_8)$alkyl, $(C_2-C_8)$alkenyl, $(C_2-C_8)$alkynyl, $(C_7-C_{12})$arylalkyl, $(C_7-C_{12})$alkylaryl, $(C_3-C_8)$cycloalkyl, $(C_3-C_8)$cycloalkenyl, phenyl, toluyl, xylenyl, benzyl, biphenyl, $(C_1-C_8)$alkoxy, $(C_2-C_8)$alkenyloxy, $(C_2-C_8)$alkynyloxy, $(C_2-C_{12})$alkoxyalkyl, $(C_2-C_{12})$alkoxyalkyloxy, $(C_2-C_{12})$alkylcarbonyl, $(C_2-C_{12})$alkylcarbonylamino, $(C_2-C_{12})$alkoxyamino, $(C_2-C_{12})$alkoxyaminocarbonyl, $(C_1-C_{12})$alkylamino, $(C_1-C_6)$alkylthio, $(C_2-C_{12})$alkylthiocarbonyl, $(C_1-C_8)$alkylsulfinyl, $(C_1-C_8)$alkylsulfonyl, $(C_2-C_8)$haloalkoxy, $(C_1-C_8)$haloalkylsulfonyl, $(C_2-C_8)$haloalkyl, $C_1-C_8)$hydroxyalkyl, —C(O)O($C_1-C_8$ alkyl), —(CH$_2$)$_n$—O—(C$_1$–C$_8$)alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8; and R is $(C_1-C_4)$alkyl, phenyl or $(C_7-C_{12})$aryl.

9. A compound selected from the group consisting of:
(5-benzyl-10-carbamoyl-5,6,7,8,9,10-hexahydro-cyclohept[b]indol-1-yloxy)-acetic acid,
(5-[(2-phenoxyphenyl)methyl]-10-carbamoyl-5,6,7,8,9,10-hexahydro-cyclohept[b]indol-1-yloxy)-acetic acid,
(5-[(3-phenoxyphenyl)methyl]-10-carbamoyl-5,6,7,8,9,10-hexahydro-cyclohept[b]indol-1-yloxy)-acetic acid,
(5-[(4-phenoxyphenyl)methyl]-10-carbamoyl-5,6,7,8,9,10-hexahydro-cyclohept[b]indol-1-yloxy)-acetic acid,
(5-[(2-fluorophenyl)methyl]-10-carbamoyl-5,6,7,8,9,10-hexahydro-cyclohept[b]indol-1-yloxy)-acetic acid,
(5-[(3-fluorophenyl)methyl]-10-carbamoyl-5,6,7,8,9,10-hexahydro-cyclohept[b]indol-1-yloxy)-acetic acid,
(5-[(4-fluorophenyl)methyl]-10-carbamoyl-5,6,7,8,9,10-hexahydro-cyclohept[b]indol-1-yloxy)-acetic acid,
(5-[(2-chlorophenyl)methyl]-10-carbamoyl-5,6,7,8,9,10-hexahydro-cyclohept[b]indol-1-yloxy)-acetic acid,
(5-[(3-chlorophenyl)methyl]-10-carbamoyl-5,6,7,8,9,10-hexahydro-cyclohept[b]indol-1-yloxy)-acetic acid,
(5-[(4-chlorophenyl)methyl]-10-carbamoyl-5,6,7,8,9,10-hexahydro-cyclohept[b]indol-1-yloxy)-acetic acid,
(5-[(2-bromophenyl)methyl]-10-carbamoyl-5,6,7,8,9,10-hexahydro-cyclohept[b]indol-1-yloxy)-acetic acid,
(5-[(3-bromophenyl)methyl]-10-carbamoyl-5,6,7,8,9,10-hexahydro-cyclohept[b]indol-1-yloxy)-acetic acid,
(5-[(4-bromophenyl)methyl]-10-carbamoyl-5,6,7,8,9,10-hexahydro-cyclohept[b]indol-1-yloxy)-acetic acid,
(5-[(2-iodophenyl)methyl]-10-carbamoyl-5,6,7,8,9,10-hexahydro-cyclohept[b]indol-1-yloxy)-acetic acid,
(5-[(3-iodophenyl)methyl]-10-carbamoyl-5,6,7,8,9,10-hexahydro-cyclohept[b]indol-1-yloxy)-acetic acid,
(5-[(4-iodophenyl)methyl]-10-carbamoyl-5,6,7,8,9,10-hexahydro-cyclohept[b]indol-1-yloxy)-acetic acid,
(5-[(2-acetamidophenyl)methyl]-10-carbamoyl-5,6,7,8,9,10-hexahydro-cyclohept[b]indol-1-yloxy)-acetic acid,
(5-[(3-acetamidophenyl)methyl]-10-carbamoyl-5,6,7,8,9,10-hexahydro-cyclohept[b]indol-1-yloxy)-acetic acid,
(5-[(4-acetamidophenyl)methyl]-10-carbamoyl-5,6,7,8,9,10-hexahydro-cyclohept[b]indol-1-yloxy)-acetic acid,
(5-[(2-carbamoylphenyl)methyl]-10-carbamoyl-5,6,7,8,9,10-hexahydro-cyclohept[b]indol-1-yloxy)-acetic acid,
(5-[(3-carbamoylphenyl)methyl]-10-carbamoyl-5,6,7,8,9,10-hexahydro-cyclohept[b]indol-1-yloxy)-acetic acid,
(5-[(4-carbamoylphenyl)methyl]-10-carbamoyl-5,6,7,8,9,10-hexahydro-cyclohept[b]indol-1-yloxy)-acetic acid,
(5-[(2-methylsulfonylphenyl)methyl]-10-carbamoyl-5,6,7,8,9,10-hexahydro-cyclohept[b]indol-1-yloxy)-acetic acid,
(5-[(3-methylsulfonylphenyl)methyl]-10-carbamoyl-5,6,7,8,9,10-hexahydro-cyclohept[b]indol-1-yloxy)-acetic acid,
(5-[(4-methylsulfonylphenyl)methyl]-10-carbamoyl-5,6,7,8,9,10-hexahydro-cyclohept[b]indol-1-yloxy)-acetic acid,
(5-[(2-methylphenyl)methyl]-10-carbamoyl-5,6,7,8,9,10-hexahydro-cyclohept[b]indol-1-yloxy)-acetic acid,
(5-[(3-methylphenyl)methyl]-0-carbamoyl-5,6,7,8,9,10-hexahydro-cyclohept[b]indol-1-yloxy)-acetic acid,
(5-[(4-methylphenyl)methyl]-10-carbamoyl-5,6,7,8,9,10-hexahydro-cyclohept[b]indol-1-yloxy)-acetic acid,
(5-[(2-ethylphenyl)methyl]-10-carbamoyl-5,6,7,8,9,10-hexahydro-cyclohept[b]indol-1-yloxy)-acetic acid,
(5-[(3-ethylphenyl)methyl]-10-carbamoyl-5,6,7,8,9,10-hexahydro-cyclohept[b]indol-1-yloxy)-acetic acid,
(5-[(4-ethylphenyl)methyl]-10-carbamoyl-5,6,7,8,9,10-hexahydro-cyclohept[b]indol-1-yloxy)-acetic acid,
(5-[(2-trifluoromethylphenyl)methyl]-10-carbamoyl-5,6,7,8,9,10-hexahydro-cyclohept[b]indol-1-yloxy)-acetic acid,
(5-[(3-trifluoromethylphenyl)methyl]-10-carbamoyl-5,6,7,8,9,10-hexahydro-cyclohept[b]indol-1-yloxy)-acetic acid,
(5-[(4-trifluoromethylphenyl)methyl]-10-carbamoyl-5,6,7,8,9,10-hexahydro-cyclohept[b]indol-1-yloxy)-acetic acid,
(5-[(cyclopropylphenyl)methyl]-10-carbamoyl-5,6,7,8,9,10-hexahydro-cyclohept[b]indol-1-yloxy)-acetic acid,
(5-[(cyclobutylphenyl)methyl]-10-carbamoyl-5,6,7,8,9,10-hexahydro-cyclohept[b]indol-1-yloxy)-acetic acid,
(5-[(cyclopentylphenyl)methyl]-10-carbamoyl-5,6,7,8,9,10-hexahydro-cyclohept[b]indol-1-yloxy)-acetic acid,
(5-[(cycloheptylphenyl)methyl]-10-carbamoyl-5,6,7,8,9,10-hexahydro-cyclohept[b]indol-1-yloxy)-acetic acid, (5-[(2-methoxyphenyl)methyl]-10-carbamoyl-5,6,7,8,9,10-hexahydro-cyclohept[b]indol-1-yloxy)-acetic acid,
(5-[(3-methoxyphenyl)methyl]-10-carbamoyl-5,6,7,8,9,10-hexahydro-cyclohept[b]indol-1-yloxy)-acetic acid,
(5-[(4-methoxyphenyl)methyl]-10-carbamoyl-5,6,7,8,9,10-hexahydro-cyclohept[b]indol-1-yloxy)-acetic acid,
(5-[(2-ethoxyphenyl)methyl]-10-carbamoyl-5,6,7,8,9,10-hexahydro-cyclohept[b]indol-1-yloxy)-acetic acid,
(5-[(3-ethoxyphenyl)methyl]-10-carbamoyl-5,6,7,8,9,10-hexahydro-cyclohept[b]indol-1-yloxy)-acetic acid,
(5-[(4-ethoxyphenyl)methyl]-10-carbamoyl-5,6,7,8,9,10-hexahydro-cyclohept[b]indol-1-yloxy)-acetic acid,
(5-[(2-trifluoromethoxyphenyl)methyl]-10-carbamoyl-5,6,7,8,9,10-hexahydro-cyclohept[b]indol-1-yloxy)-acetic acid,
(5-[(3-trifluoromethoxyphenyl)methyl]-10-carbamoyl-5,6,7,8,9,10-hexahydro-cyclohept[b]indol-1-yloxy)-acetic acid,
(5-[(4-trifluoromethoxyphenyl)methyl]-10-carbamoyl-5,6,7,8,9,10-hexahydro-cyclohept[b]indol-1-yloxy)-acetic acid,
(5-[(2-cyanophenyl)methyl]-10-carbamoyl-5,6,7,8,9,10-hexahydro-cyclohept[b]indol-1-yloxy)-acetic acid,
(5-[(3-cyanophenyl)methyl]-10-carbamoyl-5,6,7,8,9,10-hexahydro-cyclohept[b]indol-1-yloxy)-acetic acid,
(5-[(4-cyanophenyl)methyl]-10-carbamoyl-5,6,7,8,9,10-hexahydro-cyclohept[b]indol-1-yloxy)-acetic acid,
(5-[(2-pyridyl)methyl]-10-carbamoyl-5,6,7,8,9,10-hexahydro-cyclohept[b]indol-1-yloxy)-acetic acid,
(5-[(3-pyridyl)methyl]-10-carbamoyl-5,6,7,8,9,10-hexahydro-cyclohept[b]indol-1-yloxy)-acetic acid,
(5-[(4-pyridyl)methyl]-10-carbamoyl-5,6,7,8,9,10-hexahydro-cyclohept[b]indol-1-yloxy)-acetic acid,
(5-[(2-furyl)methyl]-10-carbamoyl-5,6,7,8,9,10-hexahydro-cyclohept[b]indol-1-yloxy)-acetic acid,
(5-[(3-furyl)methyl]-10-carbamoyl-5,6,7,8,9,10-hexahydro-cyclohept[b]indol-1-yloxy)-acetic acid,
(5-[(2-thienyl)methyl]-10-carbamoyl-5,6,7,8,9,10-hexahydro-cyclohept[b]indol-1-yloxy)-acetic acid,
(5-[(3-thienyl)methyl]-10-carbamoyl-5,6,7,8,9,10-hexahydro-cyclohept[b]indol-1-yloxy)-acetic acid,
(5-[(2-benzyl)methyl]-10-carbamoyl-5,6,7,8,9,10-hexahydro-cyclohept[b]indol-1-yloxy)-acetic acid,
(5-[(3-benzyl)methyl]-10-carbamoyl-5,6,7,8,9,10-hexahydro-cyclohept[b]indol-1-yloxy)-acetic acid,
(5-[(4-benzyl)methyl]-10-carbamoyl-5,6,7,8,9,10-hexahydro-cyclohept[b]indol-1-yloxy)-acetic acid,
(5-[(2-phenylphenyl)methyl]-10-carbamoyl-5,6,7,8,9,10-hexahydro-cyclohept[b]indol-1-yloxy)-acetic acid,
(5-[(3-phenylphenyl)methyl]-10-carbamoyl-5,6,7,8,9,10-hexahydro-cyclohept[b]indol-1-yloxy)-acetic acid,
(5-[(4-phenylphenyl)methyl]-10-carbamoyl-5,6,7,8,9,10-hexahydro-cyclohept[b]indol-1-yloxy)-acetic acid,
(5-[(1-napthyl)methyl]-10-carbamoyl-5,6,7,8,9,10-hexahydro-cyclohept[b]indol-1-yloxy)-acetic acid,
(5-[(2-napthyl)methyl]-10-carbamoyl-5,6,7,8,9,10-hexahydro-cyclohept[b]indol-1-yloxy)-acetic acid,
(5-[(2,3-difluorophenyl)methyl]-10-carbamoyl-5,6,7,8,9,10-hexahydro-cyclohept[b]indol-1-yloxy)-acetic acid,
(5-[(2,4-difluorophenyl)methyl]-10-carbamoyl-5,6,7,8,9,10-hexahydro-cyclohept[b]indol-1-yloxy)-acetic acid,
(5-[(2,5-difluorophenyl)methyl]-10-carbamoyl-5,6,7,8,9,10-hexahydro-cyclohept[b]indol-1-yloxy)-acetic acid,
(5-[(2,6-difluorophenyl)methyl]-10-carbamoyl-5,6,7,8,9,10-hexahydro-cyclohept[b]indol-1-yloxy)-acetic acid,
(5-[(3,4-difluorophenyl)methyl]-10-carbamoyl-5,6,7,8,9,10-hexahydro-cyclohept[b]indol-1-yloxy)-acetic acid,
(5-[(3,5-difluorophenyl)methyl]-10-carbamoyl-5,6,7,8,9,10-hexahydro-cyclohept[b]indol-1-yloxy)-acetic acid,
(5-[(3,6-difluorophenyl)methyl]-10-carbamoyl-5,6,7,8,9,10-hexahydro-cyclohept[b]indol-1-yloxy)-acetic acid,
(5-[(2,3-dimethylphenyl)methyl]-10-carbamoyl-5,6,7,8,9,10-hexahydro-cyclohept[b]indol-1-yloxy)-acetic acid,
(5-[(2,4-dimethylphenyl)methyl]-10-carbamoyl-5,6,7,8,9,10-hexahydro-cyclohept[b]indol-1-yloxy)-acetic acid,
(5-[(2,5-dimethylphenyl)methyl]-10-carbamoyl-5,6,7,8,9,10-hexahydro-cyclohept[b]indol-1-yloxy)-acetic acid,
(5-[(2,6-dimethylphenyl)methyl]-10-carbamoyl-5,6,7,8,9,10-hexahydro-cyclohept[b]indol-1-yloxy)-acetic acid,
(5-[(3,4-dimethylphenyl)methyl]-10-carbamoyl-5,6,7,8,9,10-hexahydro-cyclohept[b]indol-1-yloxy)-acetic acid,
(5-[(3,5-dimethylphenyl)methyl]-10-carbamoyl-5,6,7,8,9,10-hexahydro-cyclohept[b]indol-1-yloxy)-acetic acid,
(5-benzyl-10-carbamoyl-5,6,7,8,9,10-hexahydro-cyclohept[b]indol-1-yloxy)-acetic acid, methyl ester,
(5-[(2-phenoxyphenyl)methyl]-10-carbamoyl-5,6,7,8,9,10-hexahydro-cyclohept[b]indol-1-yloxy)-acetic acid, methyl ester,
(5-[(3-phenoxyphenyl)methyl]-10-carbamoyl-5,6,7,8,9,10-hexahydro-cyclohept[b]indol-1-yloxy)-acetic acid, methyl ester,
(5-[(4-phenoxyphenyl)methyl]-10-carbamoyl-5,6,7,8,9,10-hexahydro-cyclohept[b]indol-1-yloxy)-acetic acid, methyl ester,
(5-[(2-fluorophenyl)methyl]-10-carbamoyl-5,6,7,8,9,10-hexahydro-cyclohept[b]indol-1-yloxy)-acetic acid, methyl ester,
(5-[(3-fluorophenyl)methyl]-10-carbamoyl-5,6,7,8,9,10-hexahydro-cyclohept[b]indol-1-yloxy)-acetic acid, methyl ester,
(5-[(4-fluorophenyl)methyl]-10-carbamoyl-5,6,7,8,9,10-hexahydro-cyclohept[b]indol-1-yloxy)-acetic acid, methyl ester,
(5-[(2-chlorophenyl)methyl]-10-carbamoyl-5,6,7,8,9,10-hexahydro-cyclohept[b]indol-1-yloxy)-acetic acid, methyl ester,
(5-[(3-chlorophenyl)methyl]-10-carbamoyl-5,6,7,8,9,10-hexahydro-cyclohept[b]indol-1-yloxy)-acetic acid, methyl ester,
(5-[(4-chlorophenyl)methyl]-10-carbamoyl-5,6,7,8,9,10-hexahydro-cyclohept[b]indol-1-yloxy)-acetic acid, methyl ester,
(5-[(2-bromophenyl)methyl]-10-carbamoyl-5,6,7,8,9,10-hexahydro-cyclohept[b]indol-1-yloxy)-acetic acid, methyl ester,
(5-[(3-bromophenyl)methyl]-10-carbamoyl-5,6,7,8,9,10-hexahydro-cyclohept[b]indol-1-yloxy)-acetic acid, methyl ester,
(5-[(4-bromophenyl)methyl]-10-carbamoyl-5,6,7,8,9,10-hexahydro-cyclohept[b]indol-1-yloxy)-acetic acid, methyl ester,
(5-[(2-iodophenyl)methyl]-10-carbamoyl-5,6,7,8,9,10-hexahydro-cyclohept[b]indol-1-yloxy)-acetic acid, methyl ester,
(5-[(3-iodophenyl)methyl]-10-carbamoyl-5,6,7,8,9,10-hexahydro-cyclohept[b]indol-1-yloxy)-acetic acid, methyl ester, (5-[(4-iodophenyl)methyl]-10-carbamoyl-5,6,7,8,9,10-hexahydro-cyclohept[b]indol-1-yloxy)-acetic acid, methyl ester,
(5-[(2-acetamidophenyl)methyl]-10-carbamoyl-5,6,7,8,9,10-hexahydro-cyclohept[b]indol-1-yloxy)-acetic acid, methyl ester,
(5-[(3-acetamidophenyl)methyl]-10-carbamoyl-5,6,7,8,9,10-hexahydro-cyclohept[b]indol-1-yloxy)-acetic acid, methyl ester,
(5-[(4-acetamidophenyl)methyl]-10-carbamoyl-5,6,7,8,9,10-hexahydro-cyclohept[b]indol-1-yloxy)-acetic acid, methyl ester,
(5-[(2-carbamoylphenyl)methyl]-10-carbamoyl-5,6,7,8,9,10-hexahydro-cyclohept[b]indol-1-yloxy)-acetic acid, methyl ester,
(5-[(3-carbamoylphenyl)methyl]-10-carbamoyl-5,6,7,8,9,10-hexahydro-cyclohept[b]indol-1-yloxy)-acetic acid, methyl ester,
(5-[(4-carbamoylphenyl)methyl]-10-carbamoyl-5,6,7,8,9,10-hexahydro-cyclohept[b]indol-1-yloxy)-acetic acid, methyl ester,
(5-[(2-methylsulfonylphenyl)methyl]-10-carbamoyl-5,6,7,8,9,10-hexahydro-cyclohept[b]indol-1-yloxy)-acetic acid, methyl ester,
(5-[(3-methylsulfonylphenyl)methyl]-10-carbamoyl-5,6,7,8,9,10-hexahydro-cyclohept[b]indol-1-yloxy)-acetic acid, methyl ester,
(5-[(4-methylsulfonylphenyl)methyl]-10-carbamoyl-5,6,7,8,9,10-hexahydro-cyclohept[b]indol-1-yloxy)-acetic acid, methyl ester,
(5-[(2-methylphenyl)methyl]-10-carbamoyl-5,6,7,8,9,10-hexahydro-cyclohept[b]indol-1-yloxy)-acetic acid, methyl ester,
(5-[(3-methylphenyl)methyl]-10-carbamoyl-5,6,7,8,9,10-hexahydro-cyclohept[b]indol-1-yloxy)-acetic acid, methyl ester,
(5-[(4-methylphenyl)methyl]-10-carbamoyl-5,6,7,8,9,10-hexahydro-cyclohept[b]indol-1-yloxy)-acetic acid, methyl ester,
(5-[(2-ethylphenyl)methyl]-10-carbamoyl-5,6,7,8,9,10-hexahydro-cyclohept[b]indol-1-yloxy)-acetic acid, methyl ester,
(5-[(3-ethylphenyl)methyl]-10-carbamoyl-5,6,7,8,9,10-hexahydro-cyclohept[b]indol-1-yloxy)-acetic acid, methyl ester,
(5-[(4-ethylphenyl)methyl]-10-carbamoyl-5,6,7,8,9,10-hexahydro-cyclohept[b]indol-1-yloxy)-acetic acid, methyl ester,
(5-[(2-trifluoromethylphenyl)methyl]-10-carbamoyl-5,6,7,8,9,10-hexahydro-cyclohept[b]indol-1-yloxy)-acetic acid, methyl ester,
(5-[(3-trifluoromethylphenyl)methyl]-10-carbamoyl-5,6,7,8,9,10-hexahydro-cyclohept[b]indol-1-yloxy)-acetic acid, methyl ester,
(5-[(4-trifluoromethylphenyl)methyl]-10-carbamoyl-5,6,7,8,9,10-hexahydro-cyclohept[b]indol-1-yloxy)-acetic acid, methyl ester,
(5-[(cyclopropylphenyl)methyl]-10-carbamoyl-5,6,7,8,9,10-hexahydro-cyclohept[b]indol-1-yloxy)-acetic acid, methyl ester,
(5-[(cyclobutylphenyl)methyl]-10-carbamoyl-5,6,7,8,9,10-hexahydro-cyclohept[b]indol-1-yloxy)-acetic acid, methyl ester,
(5-[(cyclopentylphenyl)methyl]-10-carbamoyl-5,6,7,8,9,10-hexahydro-cyclohept[b]indol-1-yloxy)-acetic acid, methyl ester,
(5-[(cycloheptylphenyl)methyl]-10-carbamoyl-5,6,7,8,9,10-hexahydro-cyclohept[b]indol-1-yloxy)-acetic acid, methyl ester,
(5-[(2-methoxyphenyl)methyl]-10-carbamoyl-5,6,7,8,9,10-hexahydro-cyclohept[b]indol-1-yloxy)-acetic acid, methyl ester,
(5-[(3-methoxyphenyl)methyl]-10-carbamoyl-5,6,7,8,9,10-hexahydro-cyclohept[b]indol-1-yloxy)-acetic acid, methyl ester,
(5-[(4-methoxyphenyl)methyl]-10-carbamoyl-5,6,7,8,9,10-hexahydro-cyclohept[b]indol-1-yloxy)-acetic acid, methyl ester,
(5-[(2-ethoxyphenyl)methyl]-10-carbamoyl-5,6,7,8,9,10-hexahydro-cyclohept[b]indol-1-yloxy)-acetic acid, methyl ester,
(5-[(3-ethoxyphenyl)methyl]-10-carbamoyl-5,6,7,8,9,10-hexahydro-cyclohept[b]indol-1-yloxy)-acetic acid, methyl ester,
(5-[(4-ethoxyphenyl)methyl]-10-carbamoyl-5,6,7,8,9,10-hexahydro-cyclohept[b]indol-1-yloxy)-acetic acid, methyl ester,
(5-[(2-trifluoromethoxyphenyl)methyl]-10-carbamoyl-5,6,7,8,9,10-hexahydro-cyclohept[b]indol-1-yloxy)-acetic acid, methyl ester,
(5-[(3-trifluoromethoxyphenyl)methyl]-10-carbamoyl-5,6,7,8,9,10-hexahydro-cyclohept[b]indol-1-yloxy)-acetic acid, methyl ester,
(5-[(4-trifluoromethoxyphenyl)methyl]-10-carbamoyl-5,6,7,8,9,10-hexahydro-cyclohept[b]indol-1-yloxy)-acetic acid, methyl ester,
(5-[(2-cyanophenyl)methyl]-10-carbamoyl-5,6,7,8,9,10-hexahydro-cyclohept[b]indol-1-yloxy)-acetic acid, methyl ester,
(5-[(3-cyanophenyl)methyl]-10-carbamoyl-5,6,7,8,9,10-hexahydro-cyclohept[b]indol-1-yloxy)-acetic acid, methyl ester,
(5-[(4-cyanophenyl)methyl]-10-carbamoyl-5,6,7,8,9,10-hexahydro-cyclohept[b]indol-1-yloxy)-acetic acid, methyl ester,
(5-[(2-pyridyl)methyl]-10-carbamoyl-5,6,7,8,9,10-hexahydro-cyclohept[b]indol-1-yloxy)-acetic acid, methyl ester,
(5-[(3-pyridyl)methyl]-10-carbamoyl-5,6,7,8,9,10-hexahydro-cyclohept[b]indol-1-yloxy)-acetic acid, methyl ester,
(5-[(4-pyridyl)methyl]-10-carbamoyl-5,6,7,8,9,10-hexahydro-cyclohept[b]indol-1-yloxy)-acetic acid, methyl ester,
(5-[(2-furyl)methyl]-10-carbamoyl-5,6,7,8,9,10-hexahydro-cyclohept[b]indol-1-yloxy)-acetic acid, methyl ester,
(5-[(3-furyl)methyl]-10-carbamoyl-5,6,7,8,9,10-hexahydro-cyclohept[b]indol-1-yloxy)-acetic acid, methyl ester,
(5-[(2-thienyl)methyl]-10-carbamoyl-5,6,7,8,9,10-hexahydro-cyclohept[b]indol-1-yloxy)-acetic acid, methyl ester,
(5-[(3-thienyl)methyl]-10-carbamoyl-5,6,7,8,9,10-hexahydro-cyclohept[b]indol-1-yloxy)-acetic acid, methyl ester,
(5-[(2-benzyl)methyl]-10-carbamoyl-5,6,7,8,9,10-hexahydro-cyclohept[b]indol-1-yloxy)-acetic acid, methyl ester,
(5-[(3-benzyl)methyl]-10-carbamoyl-5,6,7,8,9,10-hexahydro-cyclohept[b]indol-1-yloxy)-acetic acid, methyl ester, (5-[(4-benzyl)methyl]-10-carbamoyl-5,6,7,8,9,10-hexahydro-cyclohept[b]indol-1-yloxy)-acetic acid, methyl ester,
(5-[(2-phenylphenyl)methyl]-10-carbamoyl-5,6,7,8,9,10-hexahydro-cyclohept[b]indol-1-yloxy)-acetic acid, methyl ester,
(5-[(3-phenylphenyl)methyl]-10-carbamoyl-5,6,7,8,9,10-hexahydro-cyclohept[b]indol-1-yloxy)-acetic acid, methyl ester,
(5-[(4-phenylphenyl)methyl]-10-carbamoyl-5,6,7,8,9,10-hexahydro-cyclohept[b]indol-1-yloxy)-acetic acid, methyl ester,
(5-[(1-napthyl)methyl]-10-carbamoyl-5,6,7,8,9,10-hexahydro-cyclohept[b]indol-1-yloxy)-acetic acid, methyl ester,
(5-[(2-napthyl)methyl]-10-carbamoyl-5,6,7,8,9,10-hexahydro-cyclohept[b]indol-1-yloxy)-acetic acid, methyl ester,
(5-[(2,3-difluorophenyl)methyl]-10-carbamoyl-5,6,7,8,9,10-hexahydro-cyclohept[b]indol-1-yloxy)-acetic acid, methyl ester,
(5-[(2,4-difluorophenyl)methyl]-10-carbamoyl-5,6,7,8,9,10-hexahydro-cyclohept[b]indol-1-yloxy)-acetic acid, methyl ester,
(5-[(2,5-difluorophenyl)methyl]-10-carbamoyl-5,6,7,8,9,10-hexahydro-cyclohept[b]indol-1-yloxy)-acetic acid, methyl ester,
(5-[(2,6-difluorophenyl)methyl]-10-carbamoyl-5,6,7,8,9,10-hexahydro-cyclohept[b]indol-1-yloxy)-acetic acid, methyl ester,
(5-[(3,4-difluorophenyl)methyl]-10-carbamoyl-5,6,7,8,9,10-hexahydro-cyclohept[b]indol-1-yloxy)-acetic acid, methyl ester,
(5-[(3,5-difluorophenyl)methyl]-10-carbamoyl-5,6,7,8,9,10-hexahydro-cyclohept[b]indol-1-yloxy)-acetic acid, methyl ester,
(5-[(3,6-difluorophenyl)methyl]-10-carbamoyl-5,6,7,8,9,10-hexahydro-cyclohept[b]indol-1-yloxy)-acetic acid, methyl ester,
(5-[(2,3-dimethylphenyl)methyl]-10-carbamoyl-5,6,7,8,9,10-hexahydro-cyclohept[b]indol-1-yloxy)-acetic acid, methyl ester,
(5-[(2,4-dimethylphenyl)methyl]-10-carbamoyl-5,6,7,8,9,10-hexahydro-cyclohept[b]indol-1-yloxy)-acetic acid, methyl ester,
(5-[(2,5-dimethylphenyl)methyl]-10-carbamoyl-5,6,7,8,9,10-hexahydro-cyclohept[b]indol-1-yloxy)-acetic acid, methyl ester,
(5-[(2,6-dimethylphenyl)methyl]-10-carbamoyl-5,6,7,8,9,10-hexahydro-cyclohept[b]indol-1-yloxy)-acetic acid, methyl ester,
(5-[(3,4-dimethylphenyl)methyl]-10-carbamoyl-5,6,7,8,9,10-hexahydro-cyclohept[b]indol-1-yloxy)-acetic acid, methyl ester,
(5-[(3,5-dimethylphenyl)methyl]-10-carbamoyl-5,6,7,8,9,10-hexahydro-cyclohept[b]indol-1-yloxy)-acetic acid, methyl ester,
(5-[(phenyl)methyl]-10-carbamoyl-5,6,7,8,9,10-hexahydro-cyclohept[b]indol-1-yloxy)-acetic acid, morpholinoethyl ester,
(5-[(cyclohexyl)methyl]-10-carbamoyl-5,6,7,8,9,10-hexahydro-cyclohept[b]indol-1-yloxy)-acetic acid, morpholinoethyl ester,
(5-[(cyclopentyl)methyl]-10-carbamoyl-5,6,7,8,9,10-hexahydro-cyclohept[b]indol-1-yloxy)-acetic acid, morpholinoethyl ester,
(5-[(phenyl)methyl]-10-carbamoyl-5,6,7,8,9,10-hexahydro-cyclohept[b]indol-1-yloxy)-acetic acid, N,N-diethylacetamido ester,
(5-[(cyclohexyl)methyl]-10-carbamoyl-5,6,7,8,9,10-hexahydro-cyclohept[b]indol-1-yloxy)-acetic acid, N,N-diethylacetamido ester, and
(5-[(cyclopentyl)methyl]-10-carbamoyl-5,6,7,8,9,10-hexahydro-cyclohept[b]indol-1-yloxy)-acetic acid, N,N-diethylacetamido ester.

10. The Compound of claim 1 wherein the prodrug is the methyl or ethyl or N-methylmorpholino ester of a compound of formula (I).

11. The compound of claim 1 wherein $R_1$ is the group, —($L_a$)-(acidic group) and wherein the (acidic group) is selected from the group consisting of —COOH, —COONa, and —COOK.

12. A compound of claim 1 wherein the acid linker —($L_a$)— for $R_1$ is the group ―[O—$CH_2$]―.

13. A tricyclic compound represented by the formulae (C1), (C2), or (C3):

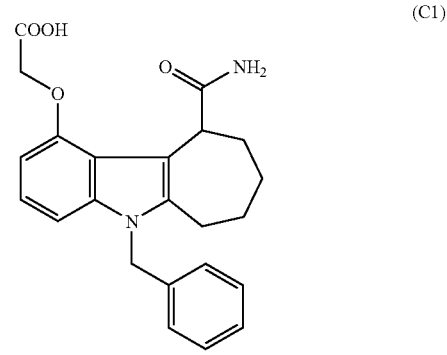

(C1)

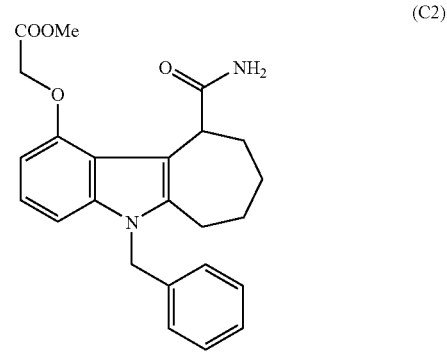

(C2)

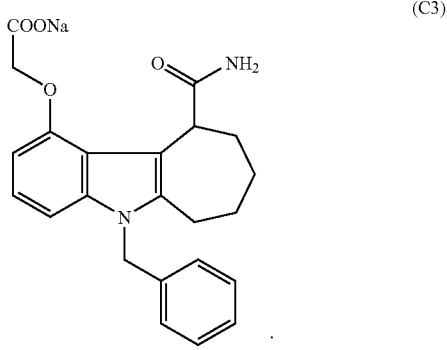

(C3)

14. A pharmaceutical formulation comprising a tricyclic compound of formula I together with a pharmaceutically acceptable carrier or diluent.

15. A method of inhibiting sPLA$_2$ mediated release of fatty acid comprising contacting sPLA$_2$ with a therapeutically effective amount of tricyclic compound of formula I for the treatment of inflammation in a mammal, wherein the method comprises administering to said mammal a therapeutically effective amount of a tricyclic compound according to claim 1.

16. A pharmaceutical formulation comprising a therapeutically effective amount of the compound of claim 1 useful for the treatment and/or amelioration of inflammatory diseases selected from the group consisting of inflammatory bowel disease, sepsis, septic shock, adult respiratory distress syndrome, pancreatitus, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, and gout.

* * * * *